(12) United States Patent
Dalerba et al.

(10) Patent No.: US 12,115,140 B2
(45) Date of Patent: Oct. 15, 2024

(54) METHOD OF TREATING ADENOID CYSTIC CARCINOMA

(71) Applicant: THE TRUSTEES OF COLUMBIA UNIVERSITY IN THE CITY OF NEW YORK, New York, NY (US)

(72) Inventors: Piero D. Dalerba, New York, NY (US); Sara Viragova, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 137 days.

(21) Appl. No.: 17/391,853

(22) Filed: Aug. 2, 2021

(65) Prior Publication Data

US 2022/0031644 A1    Feb. 3, 2022

Related U.S. Application Data

(60) Provisional application No. 63/211,940, filed on Jun. 17, 2021, provisional application No. 63/059,840, filed on Jul. 31, 2020.

(51) Int. Cl.
*A61K 31/192*    (2006.01)
*A61K 31/203*    (2006.01)

(52) U.S. Cl.
CPC .......... *A61K 31/192* (2013.01); *A61K 31/203* (2013.01)

(58) Field of Classification Search
CPC ............................ A61K 31/192; A61K 31/203
See application file for complete search history.

(56) References Cited

U.S. PATENT DOCUMENTS

| | | |
|---|---|---|
| 9,308,186 B2 | 4/2016 | Chandraratna |
| 9,949,996 B2 | 4/2018 | Chaturvedi |
| 10,213,401 B2 | 2/2019 | Chandraratna et al. |
| 10,265,378 B2 | 4/2019 | Gudas et al. |
| 10,668,039 B2 | 6/2020 | Zon et al. |

FOREIGN PATENT DOCUMENTS

| | | | |
|---|---|---|---|
| WO | WO-9808546 A2 * | 3/1998 | ............. A61K 45/06 |
| WO | WO-2012158994 A1 * | 11/2012 | ........... A61K 31/337 |
| WO | 2017201200 A1 | 11/2017 | |

OTHER PUBLICATIONS

BMS 493 Product Information Jun. 26, 2020 (Year: 2020).*
Mandelbaum et al. "Zebrafish blastomere screen identifies retinoic acid suppression of MYB in adenoid cystic carcinoma." Journal of Experimental Medicine 215.10 (2018): 2673-2685.
Hanna et al. "A phase II trial of all-trans retinoic acid (ATRA) in advanced adenoid cystic carcinoma." Oral oncology 119 (2021): 105366. (Abstract only).
Argiris et al. "A phase 2 trial of bortezomib followed by the addition of doxorubicin at progression in patients with recurrent or metastatic adenoid cystic carcinoma of the head and neck: a trial of the Eastern Cooperative Oncology Group (E1303)." Cancer 117.15 (2011): 3374-3382.
Altucci et al. "Rexinoid-Triggered Differentiation and Tumor-Selective Apoptosis of Acute Myeloid Leukemia by Protein Kinase A—Mediated Desubordination of Retinoid X Receptor." Cancer Research 65.19 (2005): 8754-8765.
Le Maire et al. "Regulation of RXR-RAR heterodimers by RXR- and RAR-specific ligands and their combinations." Cells 8.11 (2019): 1392.
Klein et al. "Identification and functional separation of retinoic acid receptor neutral antagonists and inverse agonists." Journal of Biological Chemistry 271.37 (1996): 22692-22696.
Riedl et al. "Attenuation of hypertrophy in human MSCs via treatment with a retinoic acid receptor inverse agonist." International journal of molecular sciences 21.4 (2020): 1444.
Brown et al. "Antagonizing retinoic acid receptors increases myeloid cell production by cultured human hematopoietic stem cells." Archivum immunologiae et therapiae experimentalis 65.1 (2017): 69-81.

* cited by examiner

*Primary Examiner* — Kara R McMillian
(74) *Attorney, Agent, or Firm* — BOOTH UDALL FULLER, PLC

(57) ABSTRACT

The method of treating adenoid cystic carcinoma or other cancer tumors includes the administration of an effective dosage of an inverse agonist of retinoic acid receptor (RAR) or retinoid x receptor (RXR) signaling to a patient in need thereof, alone or in combination with other cancer treatment. Non-limiting examples of an inverse agonist of retinoic acid receptor (RAR) or retinoid x receptor (RXR) signaling include 4-[(1E)-2-[5,6-Dihydro-5,5-dimethyl-8-(2-phenylethynyl)-2-naphthalenyl]ethenyl]benzoic acid (commonly referred to as "BMS493") and 4-[2-[5,6-Dihydro-5,5-dimethyl-8-(4-methylphenyl)-2-naphthalenyl] ethynyl]benzoic acid (commonly referred to as "AGN193109"). Alternatively, prior to administration of the inverse agonist of retinoic acid receptor (RAR) or retinoid x receptor (RXR) signaling, a direct agonist of retinoic acid receptor (RAR) or retinoid x receptor (RXR) signaling may be administered to the patient. Non-limiting examples of a direct agonist of retinoic acid receptor (RAR) or retinoid x receptor (RXR) signaling include all-trans retinoic acid (ATRA), isotretinoin, alitretinoin, and bexarotene.

11 Claims, 28 Drawing Sheets

METHOD OF TREATING ADENOID CYSTIC CARCINOMA

CROSS-REFERENCE TO RELATED APPLICATION

This application claims the benefit of U.S. Provisional Patent Application No. 63/211,940, filed on Jun. 17, 2021, and further claims the benefit of U.S. Provisional Patent Application No. 63/059,840, filed on Jul. 31, 2020.

GOVERNMENT LICENSE RIGHTS

This invention was made with government support under contract no. R01-DE028961 awarded by the National Institutes of Health (NIH), and under contract no. TL1-TR001875 awarded by the National Institutes of Health (NIH). The government has certain rights in the invention.

BACKGROUND

1. Field

The disclosure of the present patent application relates to cancer treatment, and particularly to a method of treating adenoid cystic carcinoma through administration of an inverse agonist of retinoic acid receptor (RAR) or retinoid x receptor (RXR) signaling to a patient in need thereof.

2. Description of the Related Art

Adenoid cystic carcinoma (ACC) is a lethal form of cancer for which there are currently no approved drug treatments. ACCs typically originate in secretory glands of the cranio-facial district, such as the salivary glands and lacrimal glands, and tend to primarily affect young and middle-aged adults. These malignancies are characterized by a high propensity toward local invasion by peri-neural infiltration (i.e., toward the invasion of surrounding tissues by dissemination along nerve sheaths) and a high propensity toward distant site metastasis (i.e., toward dissemination to other organs through blood circulation). At present, there are no systemic or targeted therapies for human ACCs which are approved by the Food and Drug Administration (FDA).

Treatment options for ACCs are typically limited to surgery and radiotherapy, both of which aim at the removal of the primary tumor and prevention of its local relapse. ACCs are usually characterized by a prolonged, yet relentless, clinical course with high mortality rates. The majority (60%) of patients affected by ACCs die within 15 years of their initial diagnosis.

From a molecular point of view, ACCs are usually characterized by low mutation rates, and are therefore considered "cold" tumors, which are unlikely to benefit from modern immunological therapies based on immune-checkpoint inhibitors (ICIs). The majority of ACCs are characterized by a t(6;9) MYB-NFIB translocation, and the majority of researchers aiming at the development of novel anti-tumor drugs for the treatment of human ACCs are focused on the discovery of pharmacological inhibitors of MYB signaling.

Although the above ongoing research has promise, effective treatments are still many years away, leaving, at present, surgery and radiotherapy. Although surgery and radiotherapy are effective with some types of cancer, the present mortality rate for patients with ACCs is still relatively high, and both surgery and radiotherapy carry their own risks, side-effects, and disadvantages. Thus, a method of treating adenoid cystic carcinoma solving the aforementioned problems is desired.

SUMMARY

The method of treating adenoid cystic carcinoma includes the administration of an effective dosage of an inverse agonist of retinoic acid receptor (RAR) or retinoid x receptor (RXR) signaling to a patient in need thereof. Non-limiting examples of an inverse agonist of retinoic acid receptor (RAR) or retinoid x receptor (RXR) signaling include 4-[(1E)-2-[5,6-Dihydro-5,5-dimethyl-8-(2-phenylethynyl)-2-naphthalenyl]ethenyl]benzoic acid (commonly, and hereinafter, referred to as "BMS493") and 4-[2-[5,6-Dihydro-5,5-dimethyl-8-(4-methylphenyl)-2-naphthalenyl]ethynyl] benzoic acid (commonly, and hereinafter, referred to as "AGN193109").

In an alternative embodiment, prior to administration of the inverse agonist of retinoic acid receptor (RAR) or retinoid x receptor (RXR) signaling, a direct agonist of retinoic acid receptor (RAR) or retinoid x receptor (RXR) signaling, or a combination of both a direct agonist of retinoic acid receptor (RAR) and a direct agonist of retinoid x receptor (RXR) signaling, may be administered to the patient. Non-limiting examples of a direct agonist of retinoic acid receptor (RAR) or retinoid x receptor (RXR) signaling include all-trans retinoic acid (ATRA), isotretinoin, alitretinoin, and bexarotene.

As a further alternative, the inverse agonist of retinoic acid receptor (RAR) or retinoid x receptor (RXR) signaling may be administered to the patient to serve as a radio-sensitizer or a chemo-sensitizer, prior to or concurrently with treating the patient with radiotherapy or chemotherapy.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
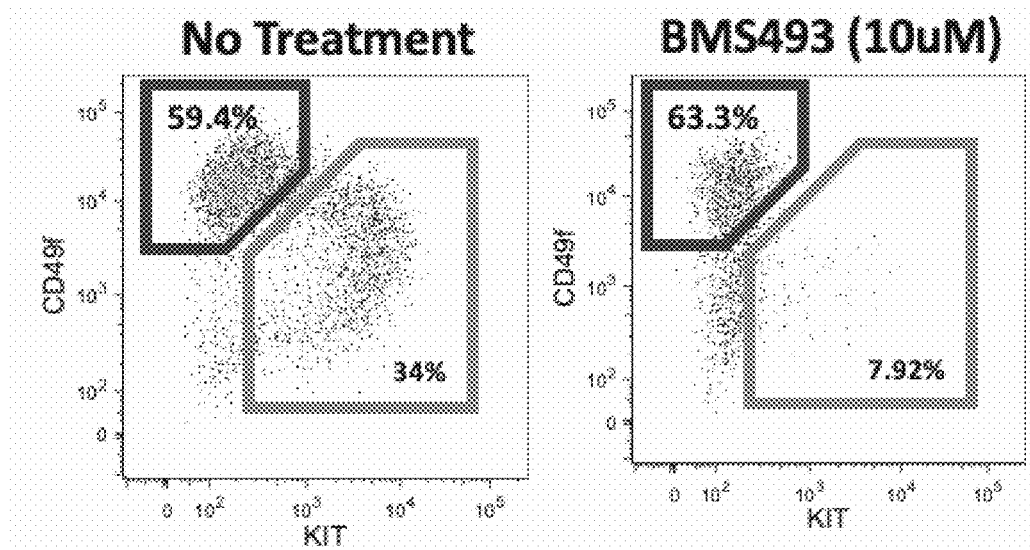
FIG. 1A shows scatter plots illustrating the relative content of myoepithelial-like cells ($CD49f^{high}$, $KIT^{neg}$) and ductal-like ($CD49f^{low}$, $KIT^+$) cells in a short-term primary culture established from a patient-derived xenograft (PDX) line representative of human ACCs with "cribriform" histology (ACCX5M1) that was either left untreated or treated in vitro with BMS493 (10 µM) for 7 days and then analyzed by flow cytometry.

The method of treating adenoid cystic carcinoma (ACC) includes the administration of an effective dosage of an inverse agonist of retinoic acid receptor (RAR) or retinoid x receptor (RXR) signaling to a patient in need thereof. Non-limiting examples of an inverse agonist of retinoic acid receptor (RAR) or retinoid x receptor (RXR) signaling include 4-[(1E)-2-[5,6-Dihydro-5,5-dimethyl-8-(2-phenylethynyl)-2-naphthalenyl] ethenyl]benzoic acid (commonly, and hereinafter, referred to as "BMS493") and 4-[2-[5,6-Dihydro-5,5-dimethyl-8-(4-methylphenyl)-2-naphthalenyl] ethynyl]benzoic acid (commonly, and hereinafter, referred to as "AGN193109").

In an alternative embodiment, prior to administration of the inverse agonist of retinoic acid receptor (RAR) or retinoid x receptor (RXR) signaling, a direct agonist of retinoic acid receptor (RAR) or retinoid x receptor (RXR) signaling, or a combination of both a direct agonist of retinoic acid receptor (RAR) and a direct agonist of retinoid x receptor (RXR) signaling may be administered to the patient. Non-limiting examples of a direct agonist of retinoic acid receptor (RAR) or retinoid x receptor (RXR) signaling include all-trans retinoic acid (ATRA), isotretinoin, alitretinoin, and bexarotene.

From a histological point of view, ACCs are usually characterized by a "bi-phasic differentiation" (i.e., the malignant tissues contain two distinct cell populations, which are commonly referred to as "myoepithelial-like" and "ductal-like" cells). A combination of cell surface markers (CD49f, KIT) have been discovered which enable the differential purification and accurate quantification of the two populations using fluorescence activated cell sorting (FACS). It has further been discovered that myoepithelial-like ($CD49f^{high}$, $KIT^{neg}$) cells are associated with more aggressive biological properties as compared to ductal-like ($CD49f^{low}$, $KIT^+$) cells when tested for their tumorigenic capacity (i.e., their capacity to sustain the formation of a new tumor upon xeno-transplantation in immuno-deficient mice). In addition to the above, the present method of treating adenoid cystic carcinoma is based on the additional discovery that direct agonists of either retinoic acid receptor (RAR) or retinoid x receptor (RXR) signaling, such as all-trans retinoic acid (ATRA) and bexarotene, can modify the cell composition of human ACCs, inducing the differentiation of myoepithelial-like cells into ductal-like cells, thus changing their relative representation in malignant tissues (i.e., reducing the percentage of myoepithelial-like cells and increasing the percentage of ductal-like cells).

With regard to the present method of treating adenoid cystic carcinoma, it has been found that treatment with BMS493 and AGN193109, two inverse agonists of RAR/RXR signaling, is able to selectively kill ductal-like ($CD49f^{low}$, $KIT^+$) cells when ACCs are cultured in vitro as three-dimensional (3D) "organoids". This novel discovery indicates that RAR/RXR signaling is not only required for the differentiation of myoepithelial-like cells into ductal-like cells, but also for the continuing survival of ductal-like cells. Thus, the use of inverse agonists of RAR/RXR signaling, such as BMS493 and AGN193109, may constitute a novel class (or genus) of pharmacological agents for the clinical treatment of human ACCs.

Figure 1B:
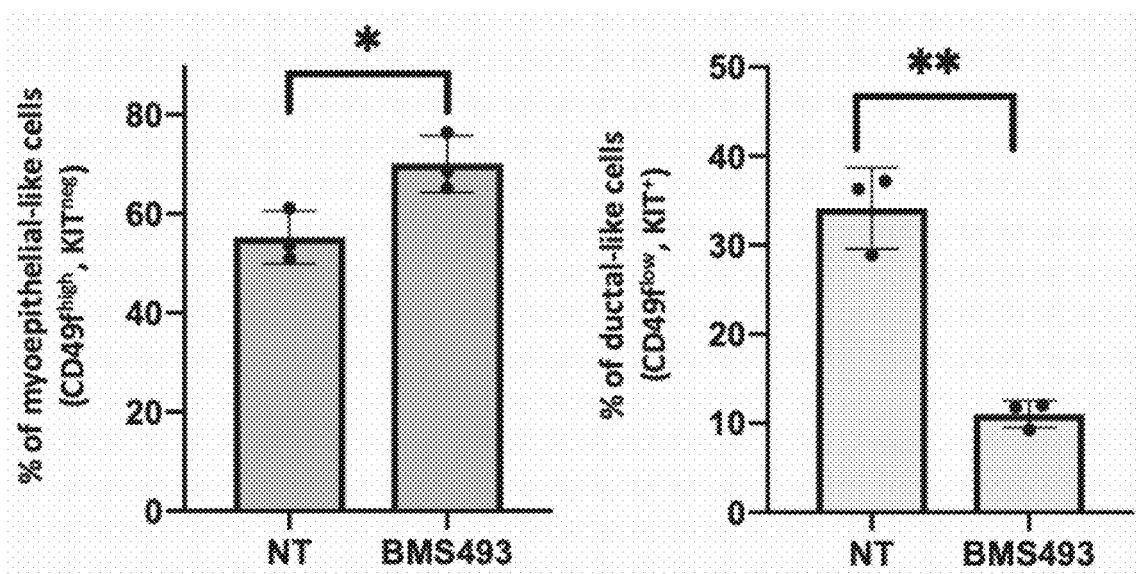
FIG. 1B shows histograms displaying the relative content of myoepithelial-like cells and ductal-like cells across 3 replicates of short-term primary cultures established from the same ACCX5M1 line of FIG. 1A that were either left untreated (NT) or treated in vitro with BMS493 (10 µM) for 7 days and then analyzed by flow cytometry.
Figure 1C:
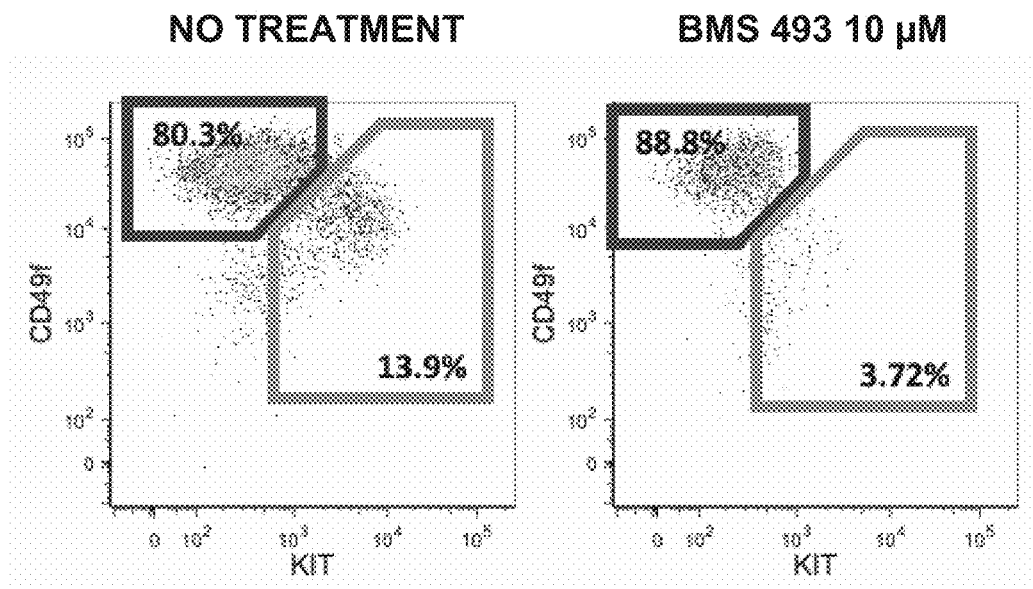
FIG. 1C shows scatter plots illustrating the relative content of myoepithelial-like cells ($CD49f^{high}$, $KIT^{neg}$) and ductal-like ($CD49f^{low}$, $KIT^+$) cells in a short-term primary culture established from a patient-derived xenograft (PDX) line representative of human ACCs with "cribriform" histology (SGTX6) that was either left untreated or treated in vitro with BM 493 (10 µM) for 7 days and then analyzed by flow cytometry.
Figure 1D:
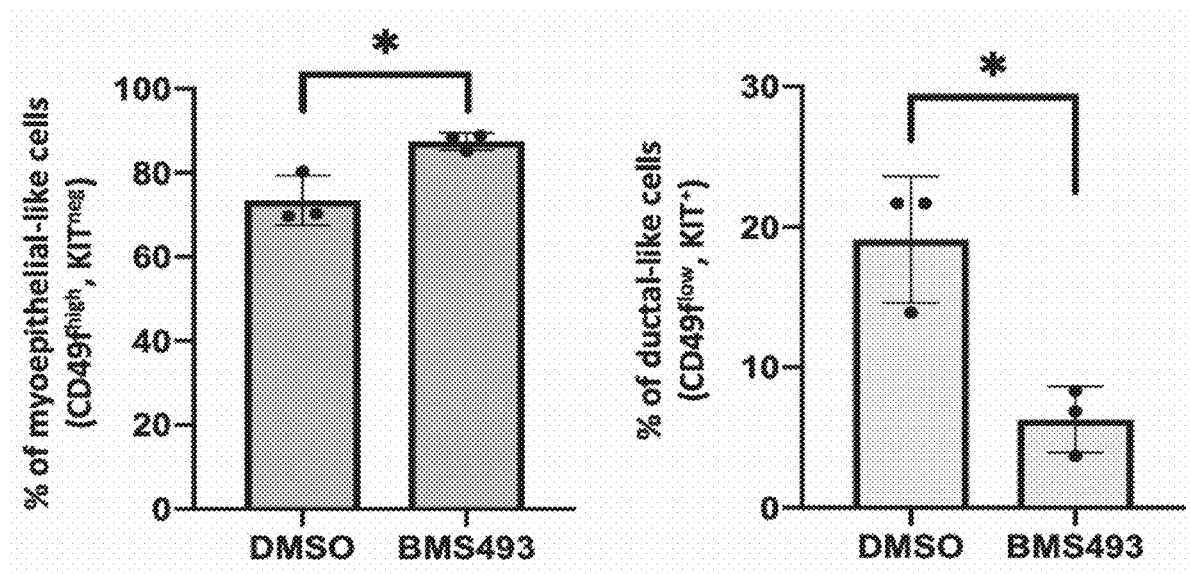
FIG. 1D shows histograms displaying the relative content of myoepithelial-like cells and ductal-like cells across 3 replicates of short-term primary cultures established from the same SGTX6 line of FIG. 1C that were either left untreated (NT) or treated in vitro with BMS493 (10 μM) for 7 days and then analyzed by flow cytometry.
Figure 1E:
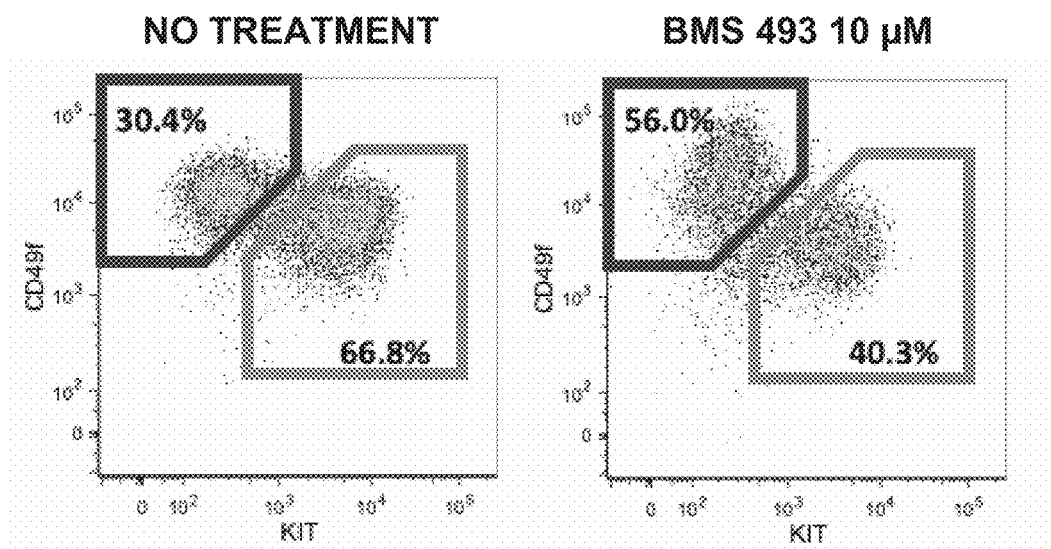
FIG. 1E shows scatter plots illustrating the relative content of myoepithelial-like cells (CD49f$^{high}$, KIT$^{neg}$) and ductal-like (CD49f$^{low}$, KIT$^{+}$) cells in a short-term primary culture established from a patient-derived xenograft (PDX) line representative of human ACCs with "cribriform" histology (ACCX6) that was either left untreated or treated in vitro with BMS493 (10 μM) for 7 days and then analyzed by flow cytometry.
Figure 1F:
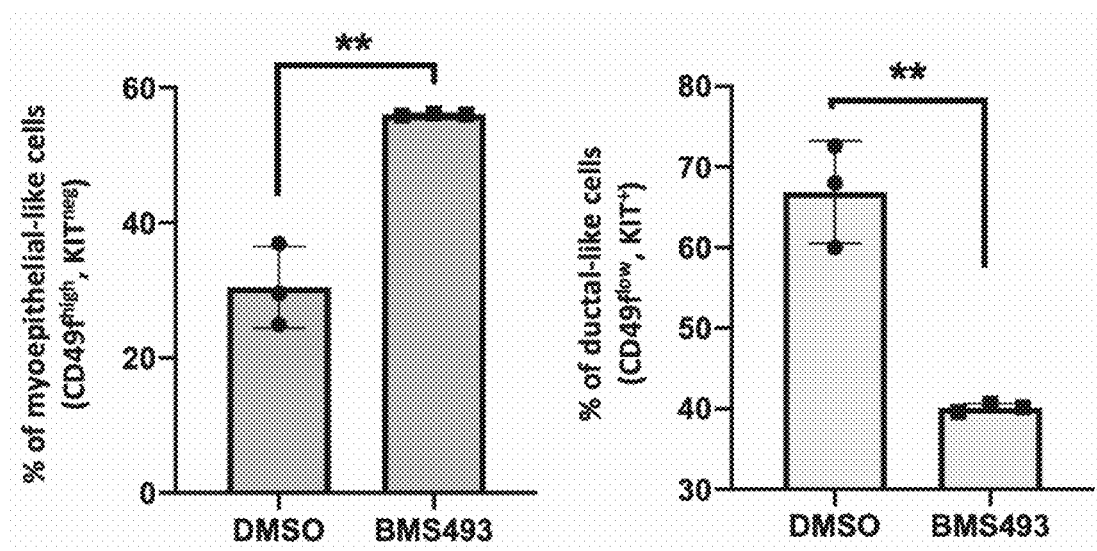
FIG. 1F shows histograms displaying the relative content of myoepithelial-like cells and ductal-like cells across 3 replicates of short-term primary cultures established from the same ACCX6 line of FIG. 1E that were either left untreated (NT) or treated in vitro with BMS493 (10 μM) for 7 days and then analyzed by flow cytometry.

With reference to FIGS. 1A-1F, 2A-2D and 3A-3I, BMS493 and AGN193109 have been shown to be effective in vitro in the 1-10 μM range. FIGS. 1A-1F and 2A-2D illustrate the in vitro anti-tumor activity of BMS493 against human ACCs. FIGS. 1A and 1B show the results of a short-term primary culture from a patient-derived xenograft (PDX) line representative of human ACCs with "cribriform" histology (ACCX5M1) treated in vitro with BMS493 (10 μM) for 7 days and then analyzed by flow cytometry. FIGS. 1C and 1D show the results of a short-term primary culture from a patient-derived xenograft (PDX) line representative of human ACCs with "cribriform" histology (SGTX6) treated in vitro with BMS493 (10 μM) for 7 days and then analyzed by flow cytometry. FIGS. 1E and 1F show the results of a short-term primary culture from a patient-derived xenograft (PDX) line representative of human ACCs with "cribriform" histology (ACCX6) treated in vitro with BMS493 (10 μM) for 7 days and then analyzed by flow cytometry.

As shown, treatment with BMS493 caused a dramatic reduction in the percentage of $CD49f^{low}$, $KIT^+$ (ductal-like) cells (green gates and green histograms), and a corresponding relative increase in the percentage of $CD49f^{high}$, $KIT^{neg}$ (myoepithelial-like) cells (red gates and red histograms; Student t-test: * $p<0.05$, ** $p<0.01$).

Figure 2A:
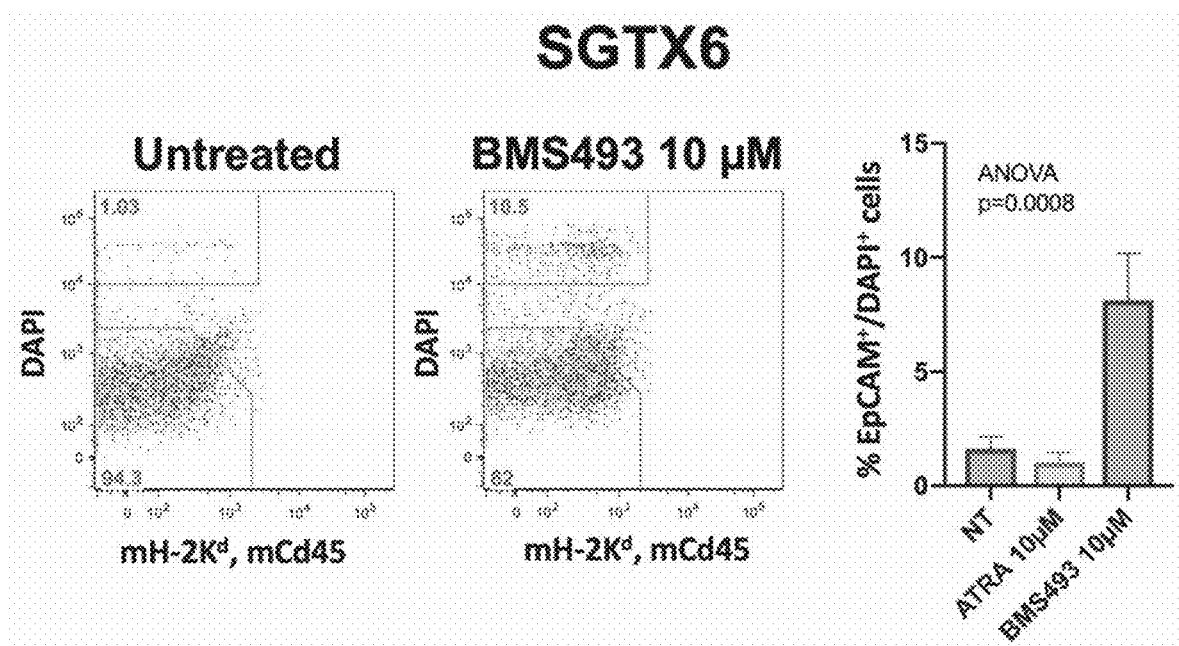
FIG. 2A shows comparison scatter plots and a comparison histogram for treatment of the SGTX6 line treated with BMS493 (10 μM) for 7 days, compared against untreated (NT) cultures and cultures treated with all-trans retinoic acid (ATRA; 10 μM).
Figure 2B:
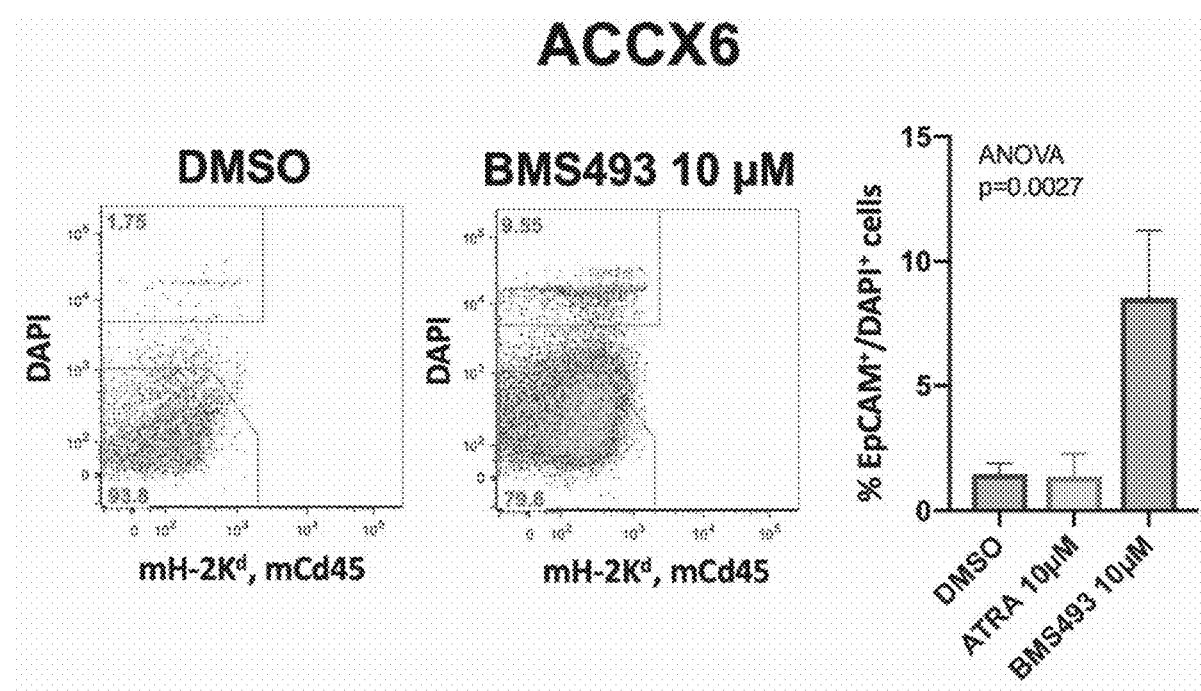
FIG. 2B shows comparison scatter plots and a comparison histogram for treatment of the ACCX6 line treated with BMS493, compared against cultures treated with dimethyl sulfoxide (DMSO) and cultures treated with all-trans retinoic acid (ATRA; 10 μM).

FIGS. 2A and 2B show scatter plots generated by flow cytometry and histograms for the SGTX6 line and the ACCX6 line, respectively, showing that the reduction in the percentage of $CD49f^{low}$, $KIT^+$ (ductal-like) cells caused by treatment with BMS493 was associated with a substantial increase in the percentage of dead tumor cells (i.e., tumor cells incorporating 4',6-diamidino-2-phenylindole or $DAPI^+$) as compared to what was observed in paired cultures that were either left untreated (NT), treated with dimethylsulfoxide (DMSO; the solvent used as a vehicle to resuspend BMS493), or treated with a retinoid agonist, such as all-trans retinoic acid (ATRA). This observation suggested a selective cytotoxic effect of BMS493 on the CD49f$^{low}$, KIT$^+$ (ductal-like) cellular component of human ACCs with "cribriform" histology. It should be noted that in FIGS. 2A and 2B, the percentage of dead tumor cells is reported as a percentage of the human epithelial cells that incorporate DAPI (i.e. EpCAM$^+$/DAPI$^+$) and excludes any contaminant of mouse cells from the primary tissues that were used to generate the cultures (i.e. excludes cells expressing H-2K$^d$ and/or mCd45).

Figure 2C:
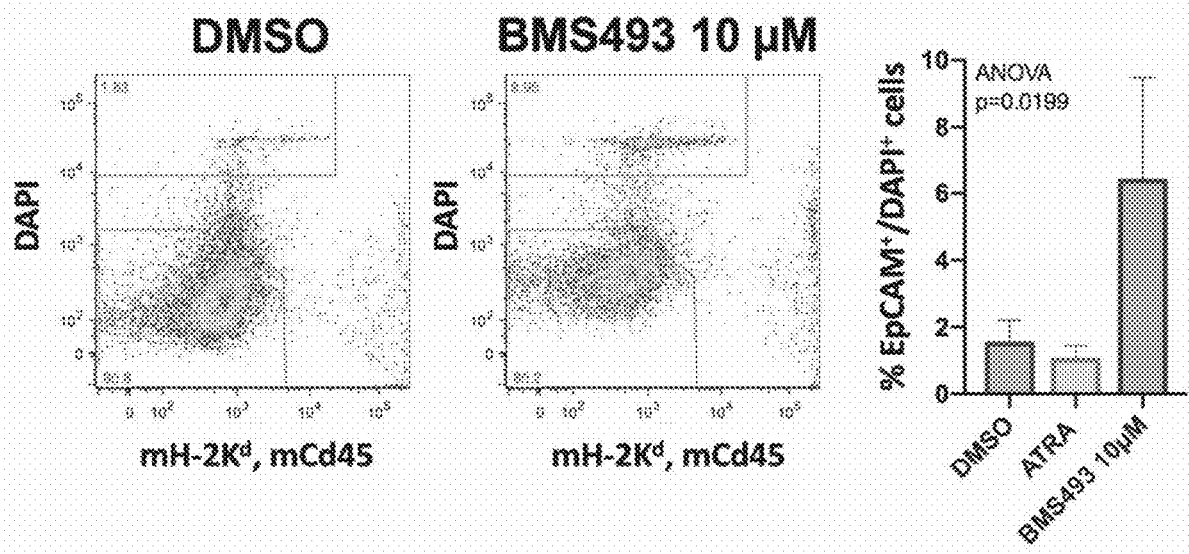
FIG. 2C shows comparison scatter plots and a comparison histogram for treatment of a short-term primary culture from an independent PDX line with "solid" histology (ACCX9), treated with BMS493, compared against cultures treated with dimethyl sulfoxide (DMSO) and cultures treated with all-trans retinoic acid (ATRA; 10 μM).
Figure 2D:
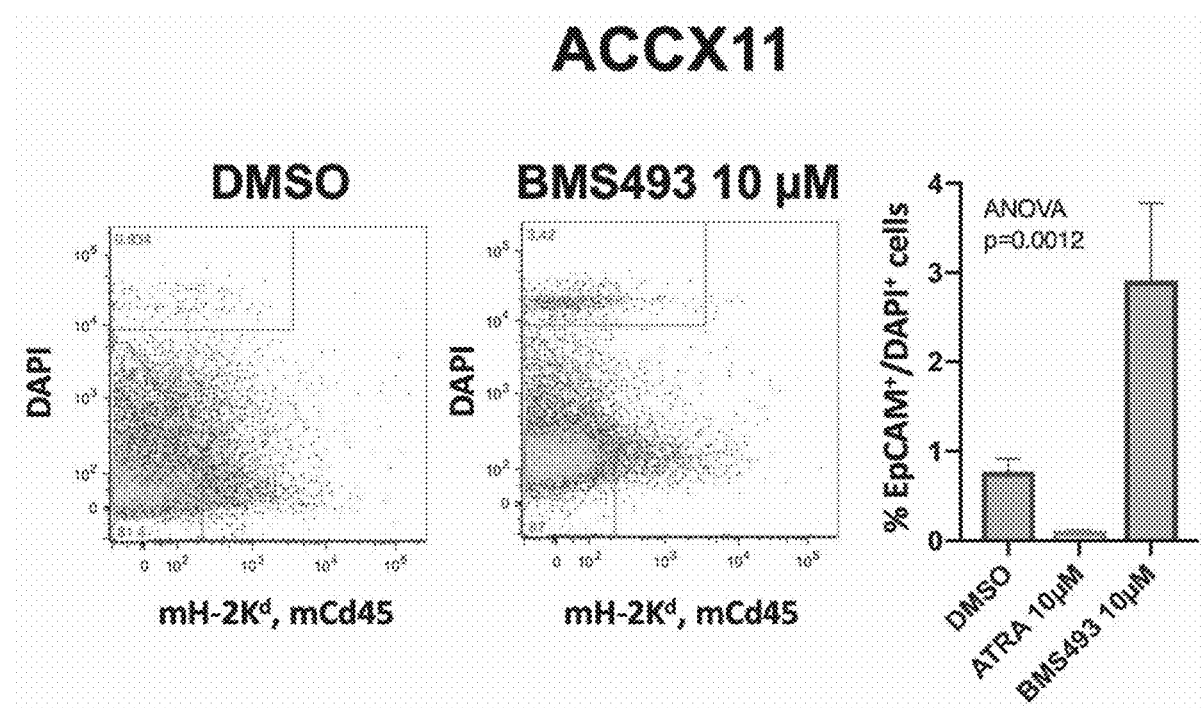
FIG. 2D shows comparison scatter plots and a comparison histogram for treatment of a short-term primary culture from an independent PDX line with "solid" histology (ACCX11), treated with BMS493, compared against cultures treated with dimethyl sulfoxide (DMSO) and cultures treated with all-trans retinoic acid (ATRA; 10 μM).

FIGS. 2C and 2D show that in vitro treatment with BMS493 also caused a substantial increase in the percentage of dead (DAPI$^+$) cells in short-term primary cultures from two additional independent PDX lines with "solid" histology (ACCX9 and ACCX11, respectively), which are representative of the most aggressive biological variant of human ACCs, and are known to be composed exclusively by CD49f$^{low}$, KIT$^+$ (ductal-like) cells. It should be noted that in FIGS. 2C and 2D, the percentage of dead tumor cells is reported as a percentage of the human epithelial cells that incorporate DAPI (i.e. EpCAM$^+$/DAPI$^+$) and excludes any contaminant of mouse cells from the primary tissues that were used to generate the cultures (i.e. excludes cells expressing H-2K$^d$ and/or mCd45).

Figure 3A:
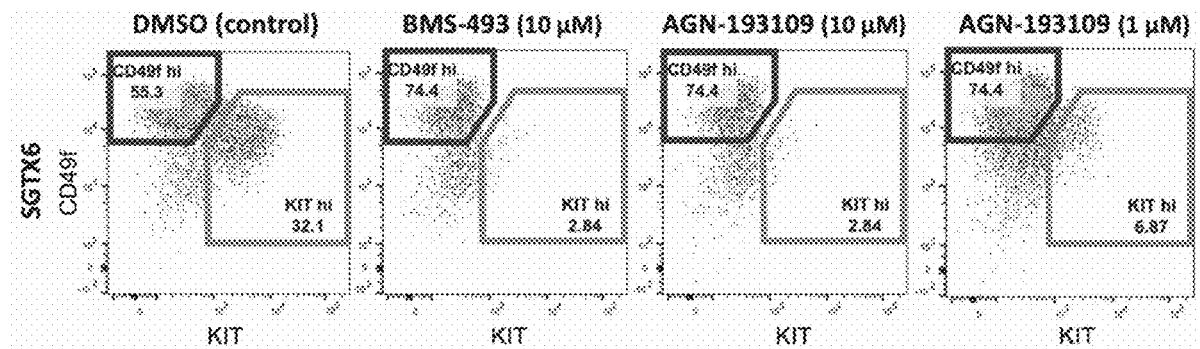
FIG. 3A shows comparison scatter plots of a short-term primary culture from a patient-derived xenograft (PDX) line representative of human ACCs with "cribriform" histology (SGTX6), which was treated in vitro for 7 days with either BMS493 or AGN193109 and then analyzed by flow cytometry.
Figure 3B:
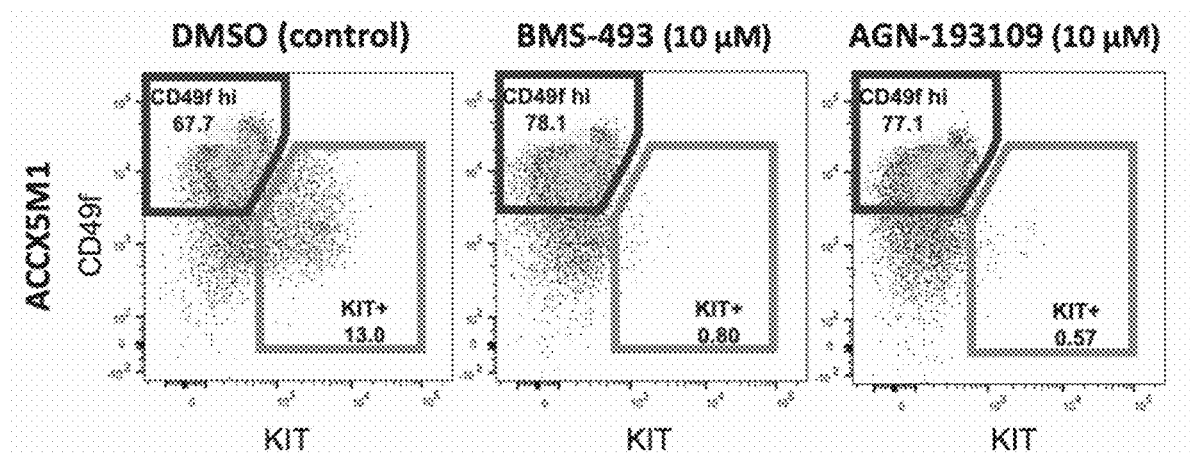
FIG. 3B shows comparison scatter plots of a short-term primary culture from a patient-derived xenograft (PDX) line representative of human ACCs with "cribriform" histology (ACCX5M1), which was treated in vitro for 7 days with either BMS493 or AGN193109 and then analyzed by flow cytometry.

FIGS. 3A-3I illustrate the in vitro anti-tumor activity of BMS493 and AGN193109 against human ACCs. FIGS. 3A and 3B show comparison plots of short-term primary cultures from two patient-derived xenograft (PDX) lines representative of human ACCs with "cribriform" histology (SGTX6 and ACCX5M1, respectively), which were treated in vitro for 7 days with either BMS493 or AGN193109 and then analyzed by flow cytometry. As shown, treatment with either drug caused a dramatic reduction in the percentage of CD49f$^{low}$, KIT$^+$ (ductal-like) cells (green gates).

Figure 3C:
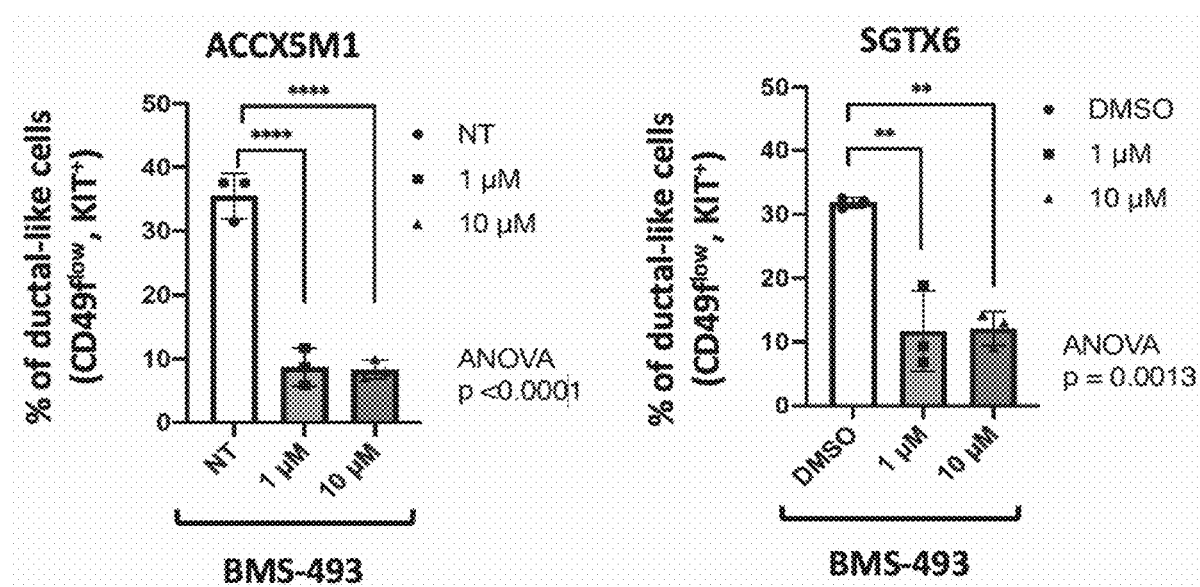
FIG. 3C shows histograms comparing the relative content of ductal-like (CD49f$^{low}$, KIT$^{+}$) cells across 3 replicates of short-term primary cultures established from the ACCX5M1 and SGTX6 lines treated with two doses of BMS493 (1 μM, 10 μM), and compared against untreated (NT) cultures and cultures treated with dimethyl sulfoxide (DMSO).
Figure 3D:
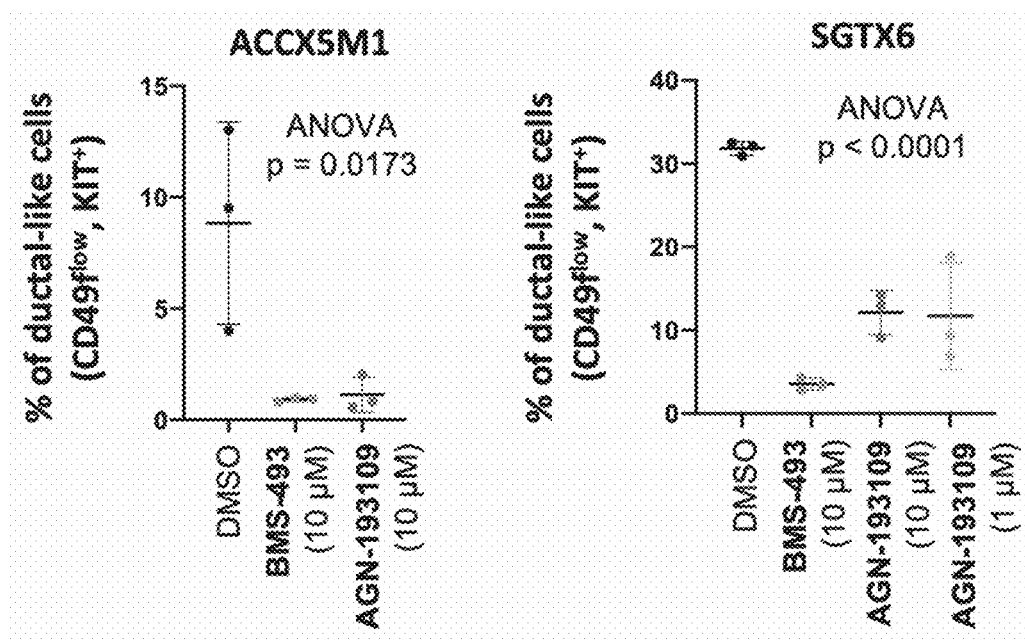
FIG. 3D shows histograms comparing the relative content of ductal-like (CD49f$^{low}$, KIT$^{+}$) cells across 3 replicates of short-term primary cultures established from the ACCX5M1 and SGTX6 lines treated with either BMS493 (10 μM) or AGN193109 (1 μM, 10 μM), and compared against cultures treated with dimethyl sulfoxide (DMSO).

FIGS. 3C and 3D are comparison histograms showing that the reduction in the percentage of CD49f$^{low}$, KIT$^+$ (ductal-like) cells observed following treatment with either BMS493 or AGN193109 was statistically significant, at both 1 μM and 10 μM concentrations, as compared to what was observed in paired cultures that were either left untreated (NT) or treated with dimethyl sulfoxide (DMSO), the solvent used as a vehicle to resuspend both BMS493 and AGN193109 (ANOVA and Student t-tests; p<0.01, **p<0.0001).

Figure 3E:
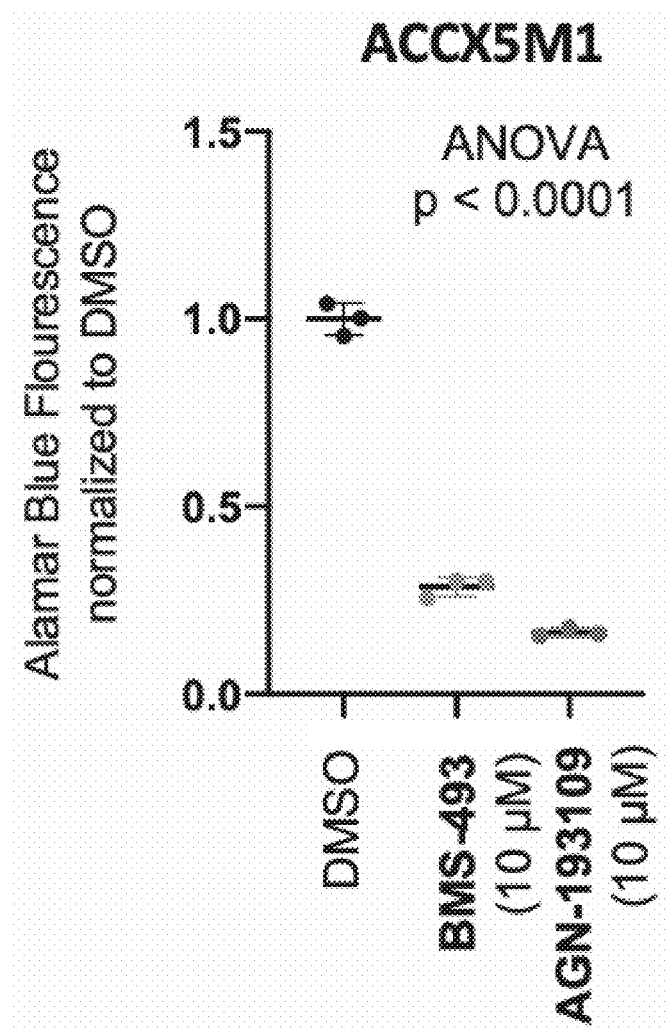
FIG. 3E shows a comparison plot for treatment of the ACCX5M1 line with BMS493 and AGN193109, compared against cultures treated with dimethyl sulfoxide (DMSO).
Figure 3F:
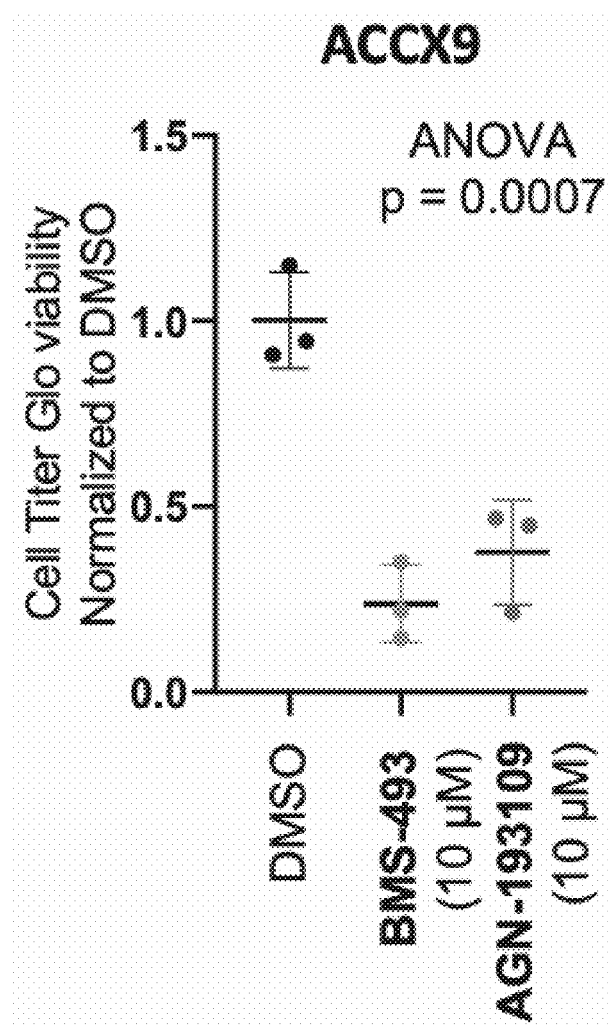
FIG. 3F shows a comparison plot for treatment of the ACCX9 line with BMS493 and AGN193109, compared against cultures treated with dimethyl sulfoxide (DMSO).

FIG. 3E shows that treatment with either BMS493 or AGN193109 was associated with reduction in cell viability as compared to control cultures (DMSO), demonstrating a selective cytotoxic activity of both drugs against the CD49f$^{low}$, KIT$^+$ (ductal-like) component of human ACCs. FIG. 3F shows that BMS493 and AGN193109 also displayed clear cytotoxic activity against primary cultures established from a PDX line with "solid" histology (ACCX9), known to be composed exclusively of CD49f$^{low}$, KIT$^+$ (ductal-like) cells. With reference to FIGS. 3E-3F, combination treatments may be used, based on the use of inverse agonists of RAR/RXR signaling (e.g., BMS493 or AGN193109) as radio-sensitizers and/or chemo-sensitizers (i.e., agents able to increase the cytotoxic activity of radiotherapy and/or chemotherapy).

Figure 3G:
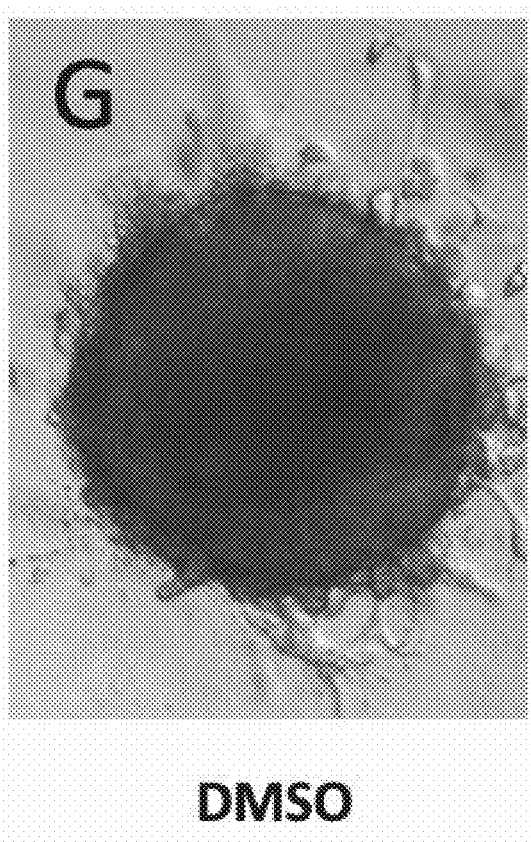
FIG. 3G is a microscope image of the ACCX9 line primary culture treated with DMSO.
Figure 3H:
FIG. 3H is a microscope image of the ACCX9 line primary culture treated with BMS493 (10 μM, 7 days).
Figure 3I:
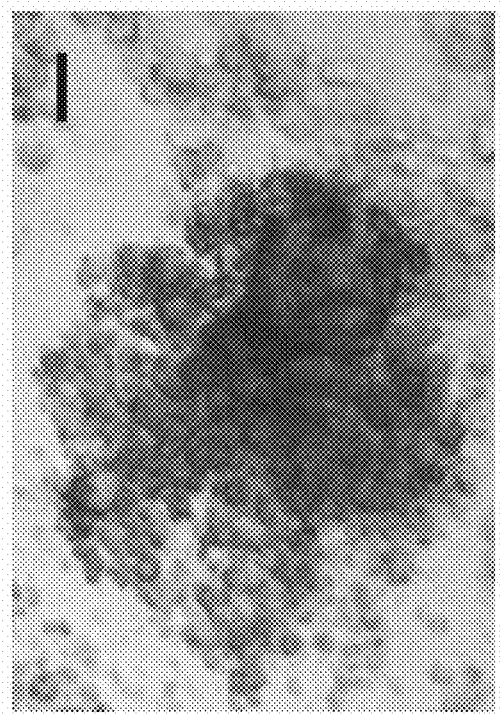
FIG. 3I is a microscope image of the ACCX9 line primary culture treated with AGN193109 (10 μM, 7 days).

FIGS. 3G, 3H and 3I are microscope images of ACCX9 primary cultures treated with DMSO, BMS493 and AGN193109, respectively. As shown, treatment with BMS493 and AGN193109 caused widespread cell fragmentation. With reference to FIGS. 3E-3F, combination treatments may be used, based on the use of inverse agonists of RAR/RXR signaling (e.g., BMS493 or AGN193109) as radio-sensitizers and/or chemo-sensitizers (i.e., agents able to increase the cytotoxic activity of radiotherapy and/or chemotherapy).

Figure 4A:
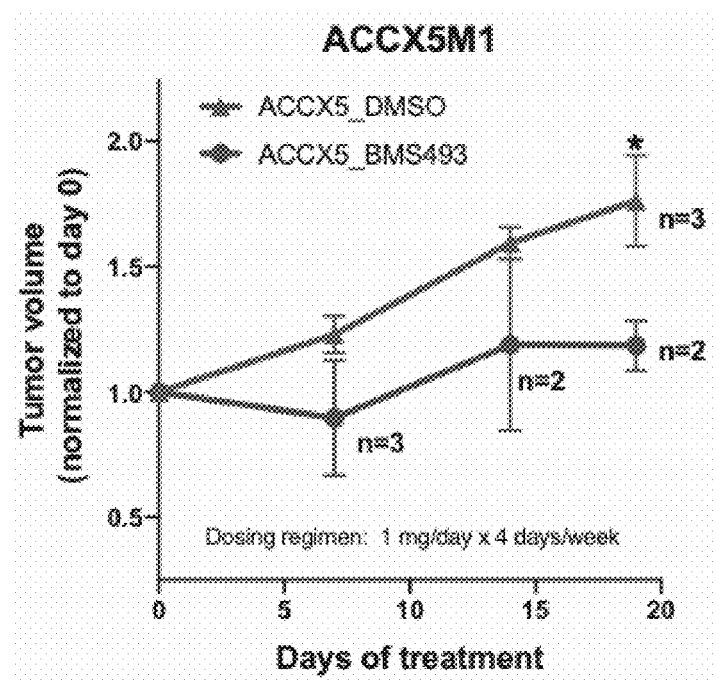
FIG. 4A is a plot comparing the in vivo growth kinetics (i.e. change in tumor volume over time) of the ACCX5M1 line following engraftment in the sub-cutaneous tissue of immune-deficient mice and treatment with BMS493, as compared against treatment with DMSO.
Figure 4B:
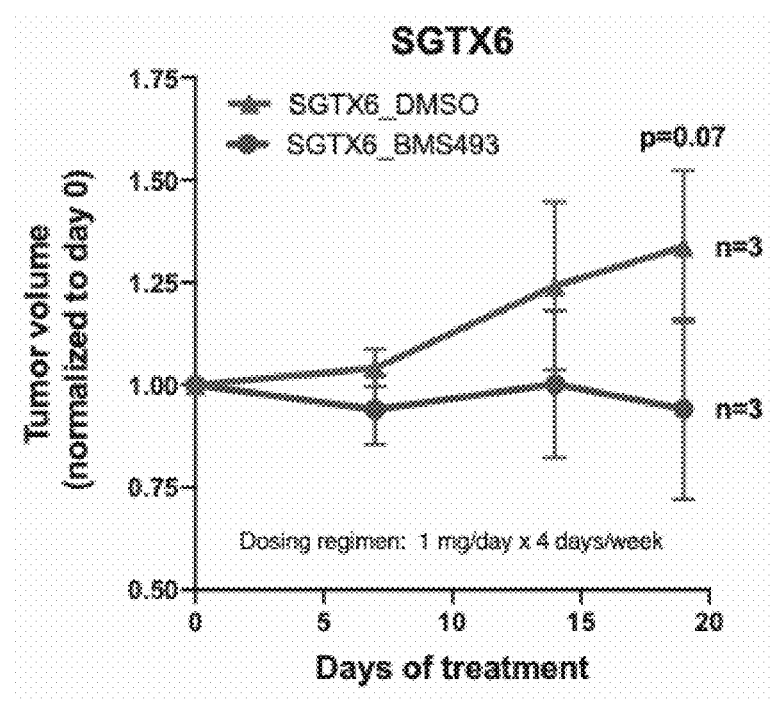
FIG. 4B is a plot comparing the in vivo growth kinetics (i.e. change in tumor volume over time) of the SGTX6 line following engraftment in the sub-cutaneous tissue of immune-deficient mice and treatment with BMS493, as compared against treatment with DMSO.
Figure 4C:
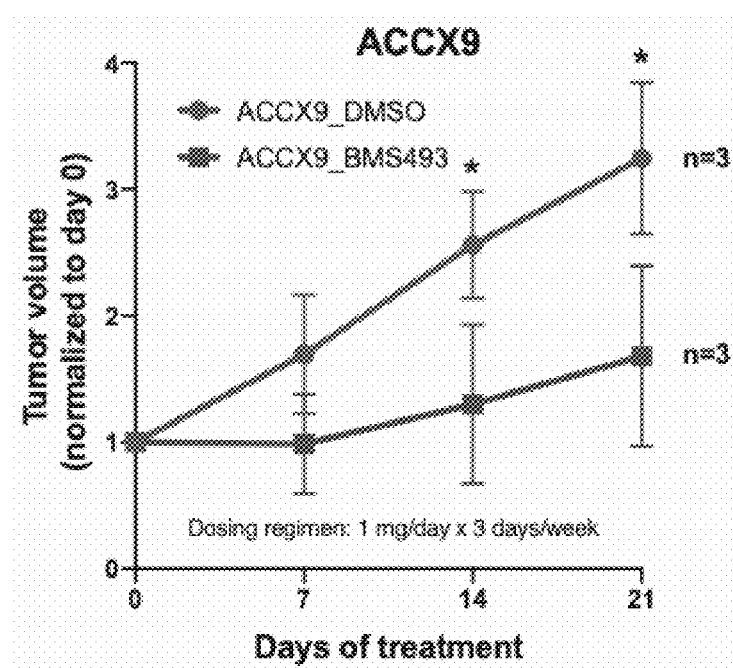
FIG. 4C is a plot comparing the in vivo growth kinetics (i.e. change in tumor volume over time) of the ACCX9 line following engraftment in the sub-cutaneous tissue of immune-deficient mice and treatment with BMS493, as compared against treatment with DMSO.

Additionally, with reference to FIGS. 4A-4C, BMS493 has been shown to be active against human ACCs engrafted in mice (in vivo) across a range of different dosing regimens, ranging from 10 mg/kg (once daily X 21 days) up to 40 mg/kg (4 times/week X 3 weeks). Three independent patient-derived xenograft (PDX) lines representative of human ACCs (ACCX5M1, SGTX6, ACCX9) were engrafted in the subcutaneous (s.c.) tissue of NOD/SCID/IL2Rγ$^{-/-}$ (NS G) immune-deficient mice and left growing until they reached a size of approximately 700 mm$^3$. Tumor-bearing mice were then divided into two cohorts, one of which was treated with BMS493 (40 mg/kg X 3-4 days/week), while the other received only DMSO (i.e., the solvent used as a vehicle to resuspend BMS493). Treatment with BMS493 was associated with either growth arrest or tumor shrinkage of all three PDX lines used for in vivo experiments.

With reference to FIGS. 5A-5F, combination treatments may be used, based on the sequential administration of direct agonists of RAR/RXR signaling (e.g., ATRA, isotretinoin, alitretinoin, or bexarotene) to induce the differentiation of myoepithelial-like cells into ductal-like cells, followed by administration of inverse agonists of RAR/RXR signaling (e.g., BMS493 or AGN193109) to permanently eliminate ductal-like cells.

FIGS. 5A-5E show that treatment of human ACC primary cultures with direct agonists of retinoic acid receptor (RAR) and retinoid x receptor (RXR) signaling causes differentiation of CD49f$^{high}$, KIT$^{neg}$ (myoepithelial-like) cells into CD49f$^{low}$, KIT$^+$ (ductal-like) cells. In short-term primary cultures established from human patient-derived xenograft (PDX) lines that are representative of human ACCs with "cribriform" histology (e.g., ACCX5M1), in vitro treatment with a direct agonist of either retinoic acid receptor (RAR) signaling, such as all-trans retinoic acid (ATRA; 10 μM), or of retinoid x receptor (RXR) signaling, such as bexarotene (10 μM), is followed by a substantial modification in cell composition, characterized by a reduction in the percentage of myoepithelial-like cells (CD49f$^{high}$, KIT$^{neg}$; red gates) and by an increase in the percentage of ductal-like cells (CD49f$^{low}$, KIT$^+$; green gates). It should be noted that in FIGS. 5D-5E, bexarotene has been abbreviated as "BEX" due to the available space in the Figures.

Figure 5A:
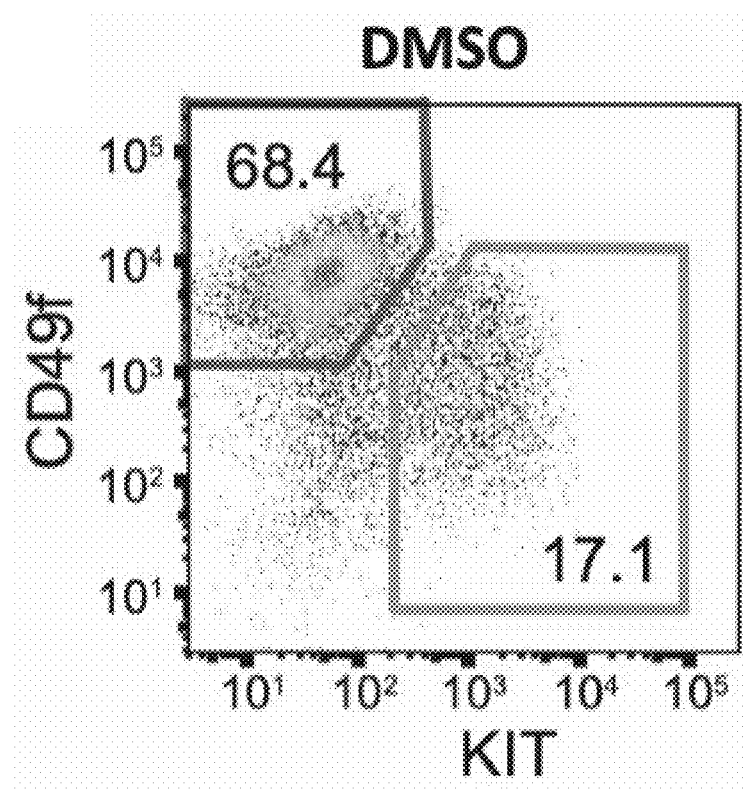
FIG. 5A is a scatter plot displaying the relative content of myoepithelial-like cells and ductal-like cells in a primary in vitro culture of the ACCX5M1 line treated with DMSO for 7 days and analyzed by flow cytometry.
Figure 5B:
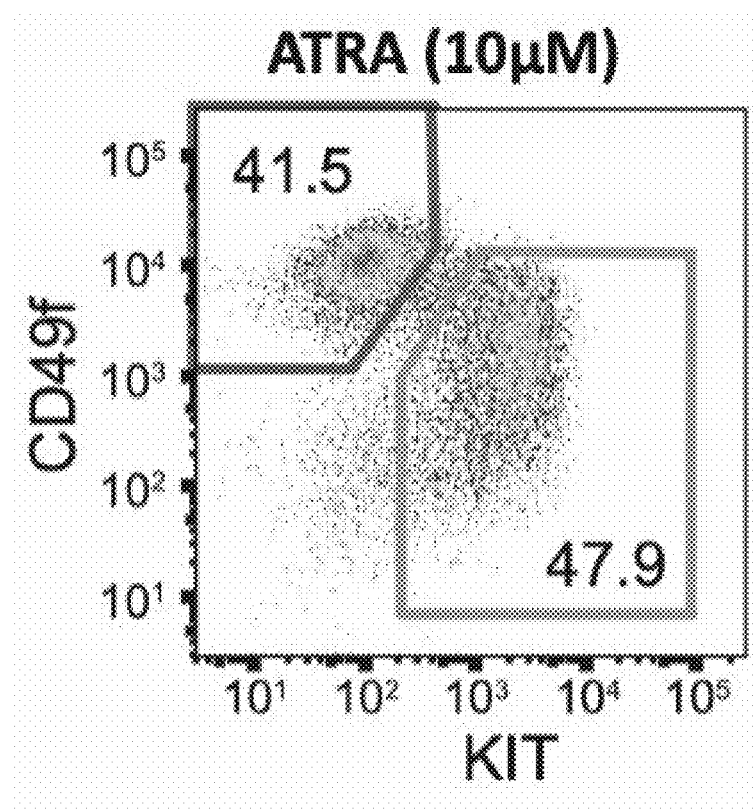
FIG. 5B is a scatter plot displaying the relative content of myoepithelial-like cells and ductal-like cells in a primary in vitro culture of the ACCX5M1 line treated with all-trans retinoic acid (ATRA; 10 μM) for 7 days and analyzed by flow cytometry.
Figure 5C:
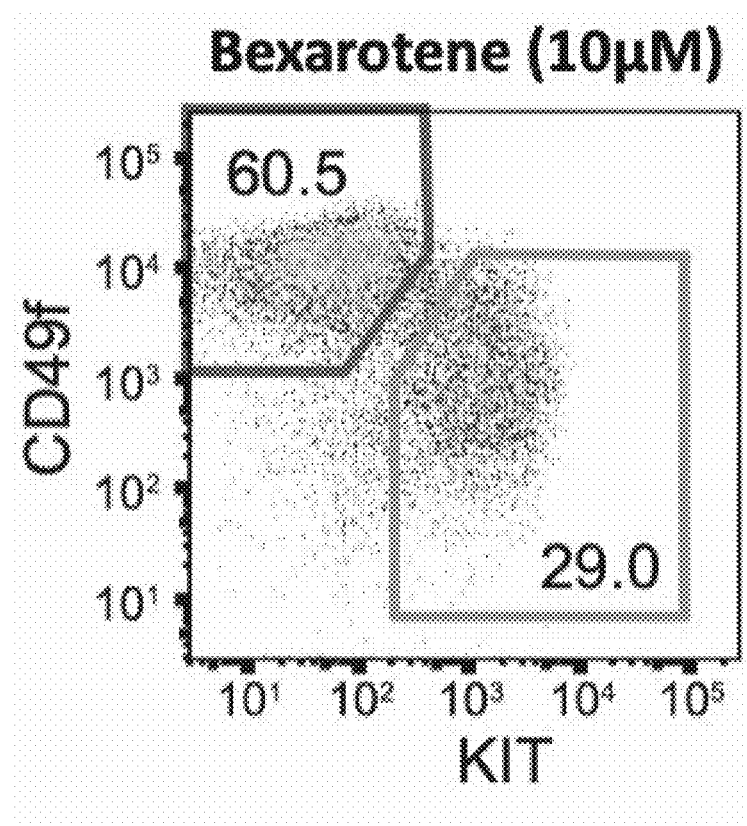
FIG. 5C is a scatter plot displaying the relative content of myoepithelial-like cells and ductal-like cells in a primary in vitro culture of the ACCX5M1 line treated with bexarotene (10 μM) for 7 days and analyzed by flow cytometry.
Figure 5D:
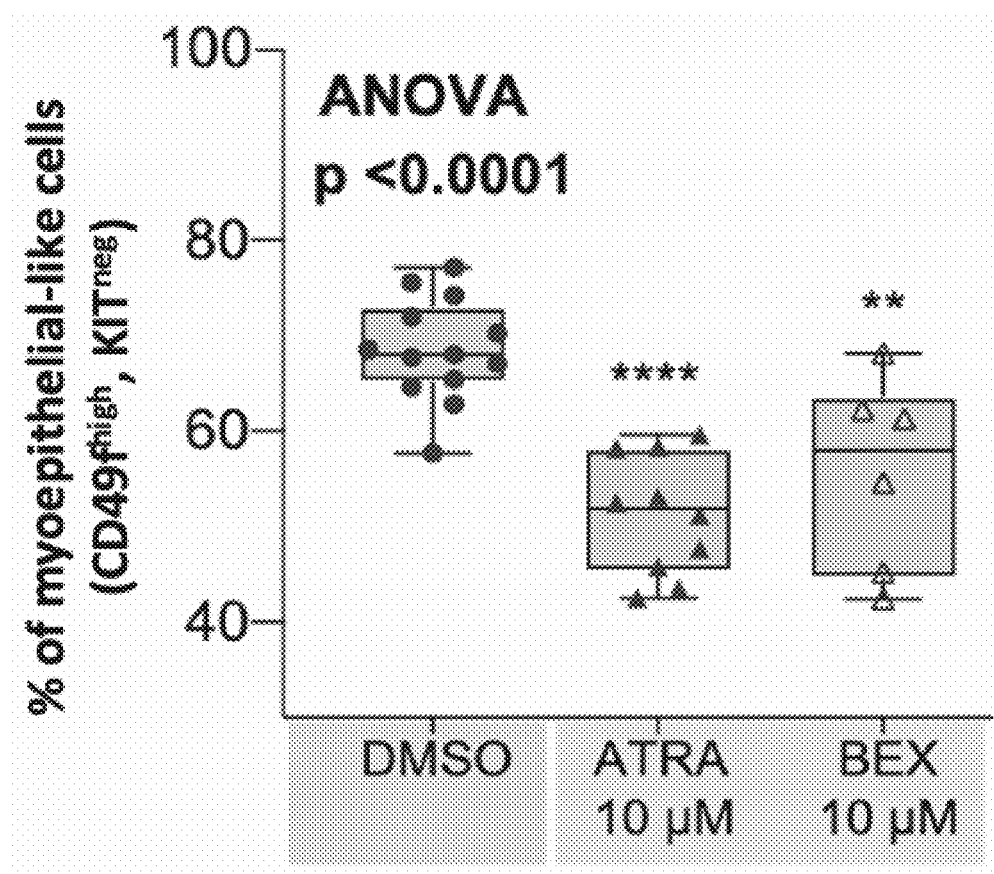
FIG. 5D is a comparison plot showing the percentage of myoepithelial-like cells following in vitro treatment of the ACCX5M1 line with DMSO, ATRA and bexarotene. It should be noted that in this figure, bexarotene has been abbreviated as "BEX" due to the available space in the Figure.
Figure 5E:
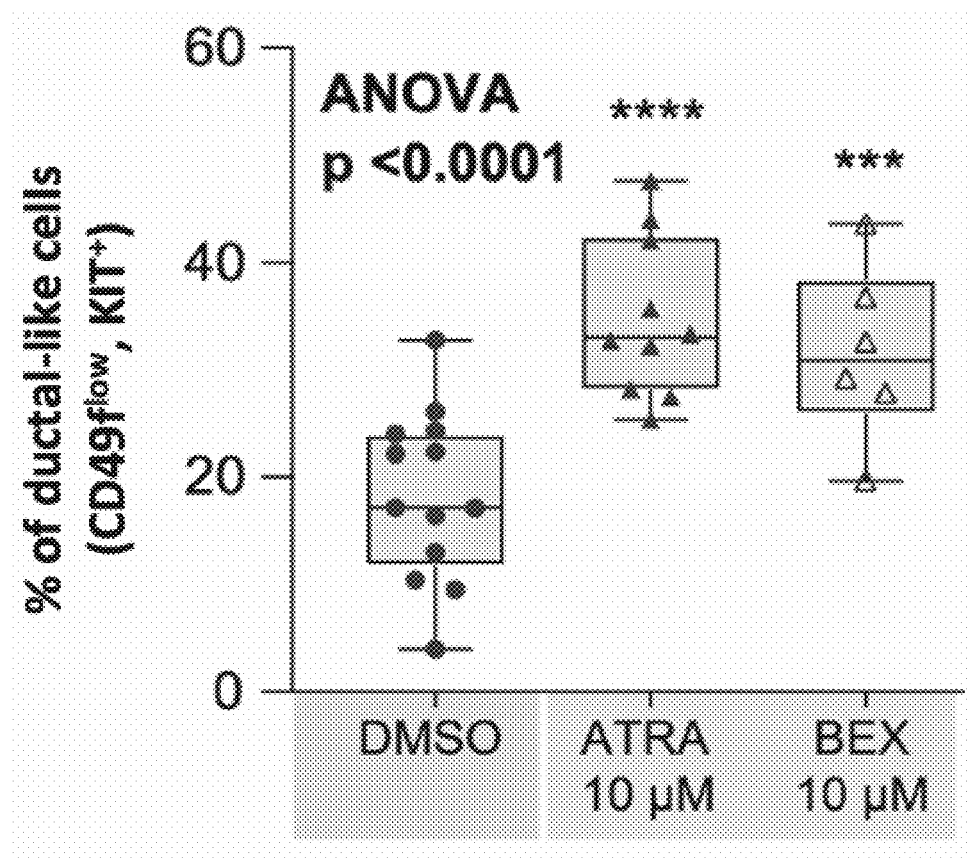
FIG. 5E is a comparison plot showing the percentage of ductal-like cells following in vitro treatment of the ACCX5M1 line with DMSO, ATRA and bexarotene. It should be noted that in this figure, bexarotene has been abbreviated as "BEX" due to the available space in the Figure.
Figure 5F:
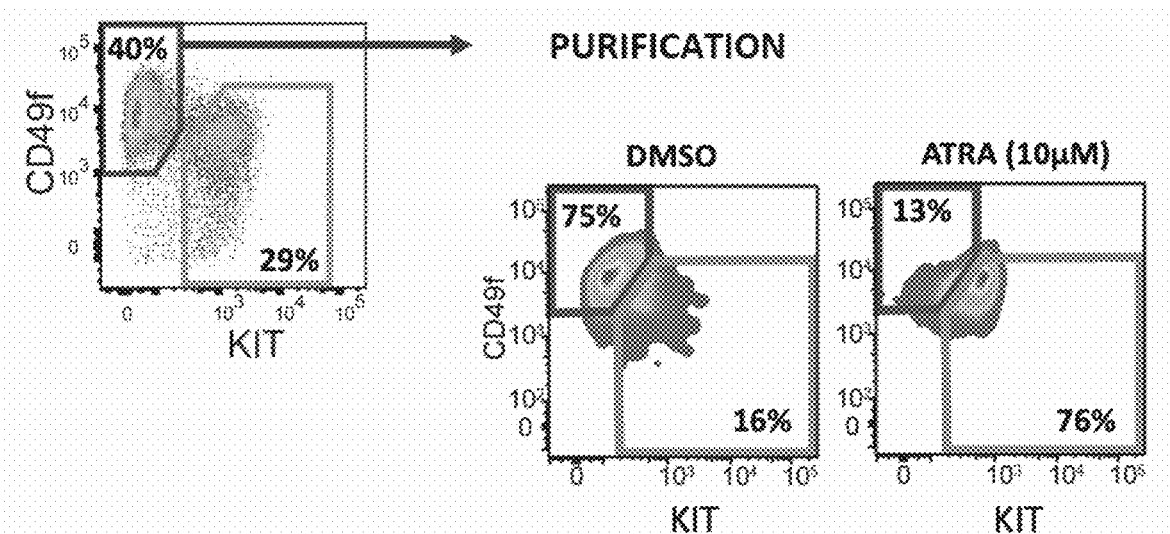
FIG. 5F illustrates the differentiation of myoepithelial-like cells into ductal-like cells through the purification of myoepithelial-like cells by fluorescence activated cell sorting (FACS) and stimulation in vitro with or without ATRA (10 mM).

FIG. 5F illustrates the differentiation of myoepithelial-like cells into ductal-like cells through the purification of myoepithelial-like cells by fluorescence activated cell sorting (FACS) and stimulation in vitro with or without ATRA (10 mM); i.e., showing that the above effect is caused by the differentiation of myoepithelial-like cells (CD49f$^{high}$, KIT$^{neg}$) into "ductal-like" cells (CD49f$^{low}$, KIT$^+$), as revealed by prospective experiments on sorted preparations of myoepithelial-like cells (CD49f$^{high}$, KIT$^{neg}$) isolated by FACS from solid tumors and treated in vitro for 7 days with a direct agonist of RAR signaling (ATRA; 10 μM).

With regard to the sequential administration of direct agonists of RAR/RXR signaling, the first step of treatment is a "differentiation" step, where the direct agonists of RAR/RXR signaling are administered to the patient. In the differentiation step, myoepithelial-like cells are forced to differentiate into ductal-like cells. The second step of treatment is an "elimination" step, where the inverse agonists of RAR/RXR signaling is administered to the patient. In the elimination step, the ductal-like cells are selectively killed. Specifically, the direct agonists of RAR/RXR signaling induce the differentiation of CD49f$^{high}$, KIT$^{neg}$ (myoepithelial-like) cells into CD49f$^{low}$, KIT$^+$ (ductal-like) cells, and that inverse agonists of RAR/RXR signaling selectively kill CD49f$^{low}$, KIT$^+$ (ductal-like) cells.

It should be understood that the method of treating adenoid cystic carcinoma further contemplates the use of inverse agonists of RAR/RXR signaling (e.g., BMS493 or AGN193109), either alone or in combination with other agents (e.g., direct agonists of RAR/RXR signaling, cytotoxic agents used in conventional chemotherapy, various forms of ionizing radiation used in radiotherapy, inhibitors of estrogen and/or androgen production or signaling used in hormone therapy, pro-differentiation agents such as inhibitors of lysine-specific de-methylases or isocitrate dehydrogenases, immune-modulatory agents used in cancer immunotherapy, anti-angiogenic agents, inhibitors of proliferative or anti-apoptotic signals mediated by tyrosine kinases, and/or inhibitors of poly(ADP-ribose) polymerases), for the treatment of all tumors that display analogies or similarities with human ACCs with regard to their origin from the salivary gland or from organs that share with the salivary gland a similar histological architecture and/or morphogenetic program during development (e.g. a branching glandular tree), or with regard to their histological and morphological appearance, or with regard to their architectural patterns of tissue growth, or with regard to their dependency on RAR/RXR signaling for cell differentiation and/or lineage specification, and/or with regard to their dependency on RAR/RXR signaling for the generation and survival of specific sub-types of malignant cells.

Non-limiting examples of tumors that display such biological similarities with human ACCs include all tumors originating from epithelial tissues (i.e., all carcinomas), including without limitation breast carcinomas, prostate carcinomas, pancreatic carcinomas, all forms of salivary gland carcinomas, lacrimal gland carcinomas, esophageal carcinomas, gastric carcinomas, cholangiocarcinomas and other carcinomas of the biliary tree, hepatocellular carcinomas, carcinomas of the small intestine, colon carcinomas, rectal carcinomas, carcinomas of the sweat glands, lung adenocarcinomas, ovarian carcinomas, carcinomas of the fallopian tubes, endometrial carcinomas, squamous cell carcinomas of the skin, head-and-neck district, lips, mouth, nasal sinuses, pharynx, larynx, esophagus, trachea, bronchi, lungs, uterine cervix, vagina, vulva, penis or anus, bladder carcinomas and other urothelial carcinomas of the renal pelvis, ureter or urethra, neuroendocrine carcinomas of the pancreas, small cell lung carcinomas, and renal cell carcinomas. These include tumors originating from epithelial secretory glands or epithelial tissues containing secretory cells, including without limitation breast carcinomas, prostate carcinomas, pancreatic carcinomas, all forms of salivary gland carcinoma, lacrimal gland carcinomas, esophageal adenocarcinomas, gastric adenocarcinomas, cholangiocarcinomas and other carcinomas of the biliary tree, carcinomas of the small intestine, colon carcinomas, rectal carcinomas, carcinomas of the sweat glands, lung adenocarcinomas, ovarian carcinomas, carcinomas of the fallopian tubes, and endometrial carcinomas. More broadly, these treatments will be useful for treating all forms of cancer (including without limitation all carcinomas, sarcomas, gliomas, neuroblastomas, melanomas, leukemias, lymphomas, testicular cancers, and mesotheliomas).

Additionally, as noted above, as a further alternative, the inverse agonist of retinoic acid receptor (RAR) or retinoid x receptor (RXR) signaling may be administered to the patient to serve as a radio-sensitizer or a chemo-sensitizer, prior to or simultaneously with treating the patient with radiotherapy or chemotherapy.

Figures 6A, 6B, 6C:
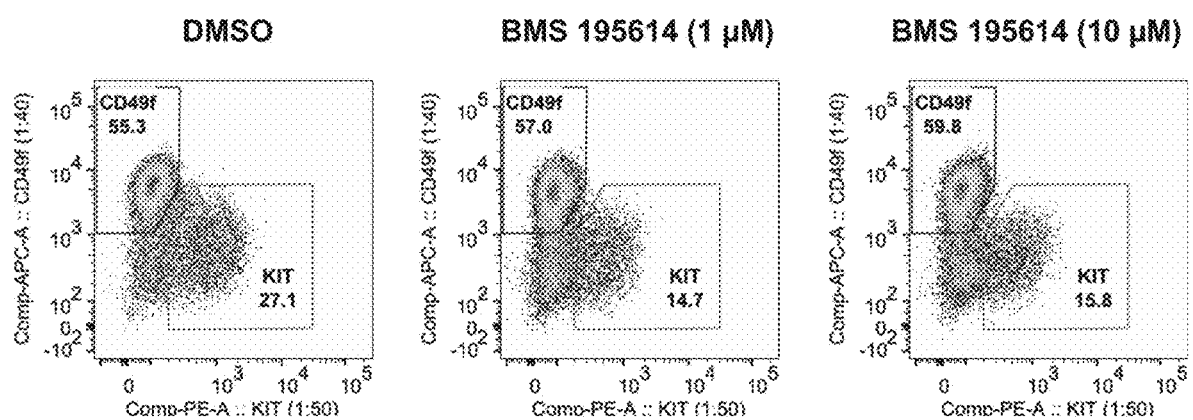
FIG. 6A is a scatter plot displaying the relative content of myoepithelial-like cells and ductal-like cells in a primary in vitro organoid culture of the ACCX5M1 patient-derived xenograft (PDX) line treated with DMSO for 7 days and analyzed by flow cytometry.
FIG. 6B is a scatter plot displaying the relative content of myoepithelial-like cells and ductal-like cells in a primary in vitro organoid culture of the ACCX5M1 patient-derived xenograft (PDX) line treated with the neutral antagonist BMS195614 (1 μM) for 7 days and analyzed by flow cytometry.
FIG. 6C is a scatter plot displaying the relative content of myoepithelial-like cells and ductal-like cells in a primary in vitro organoid culture of the ACCX5M1 patient-derived xenograft (PDX) line treated with the neutral antagonist BMS195614 (10 μM) for 7 days and analyzed by flow cytometry.

Further, as shown in FIGS. 6A-10, the efficacies of the inverse agonists BMS493 and AGN193109 were compared against a neutral antagonist (BMS195614). For FIGS. 6A-8, organoid cultures from a patient derived xenograft line (ACCX5M1) were treated for one week with DMSO (as a control), the neutral antagonist (BMS195614, 1 μM, 10 μM) or the inverse agonists (BMS493 1 μM, BMS493 10 μM, AGN193109 10 μM). The graphs display the percentage of KIT+ cells in each culture condition. FIG. 6A is a scatter plot displaying the relative content of myoepithelial-like cells and ductal-like cells in a primary in vitro organoid culture of the ACCX5M1 patient-derived xenograft (PDX) line treated with DMSO for 7 days and analyzed by flow cytometry. FIG. 6B is a scatter plot displaying the relative content of myoepithelial-like cells and ductal-like cells in a primary in vitro organoid culture of the ACCX5M1 patient-derived xenograft (PDX) line treated with the neutral antagonist BMS195614 (1 μM) for 7 days and analyzed by flow cytometry. FIG. 6C is a scatter plot displaying the relative content of myoepithelial-like cells and ductal-like cells in a primary in vitro organoid culture of the ACCX5M1 patient-derived xenograft (PDX) line treated with the neutral antagonist BMS195614 (10 μM) for 7 days and analyzed by flow cytometry.

Figure 7A:
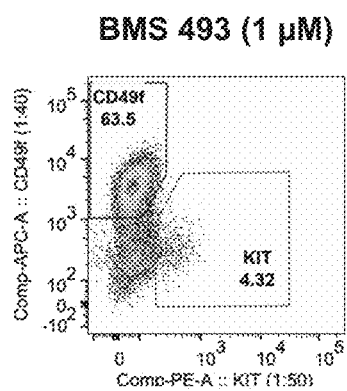
FIG. 7A is a scatter plot displaying the relative content of myoepithelial-like cells and ductal-like cells in a primary in vitro organoid culture of the ACCX5M1 patient-derived xenograft (PDX) line treated with the inverse agonist BMS493 (1 μM) for 7 days and analyzed by flow cytometry.
Figure 7B:
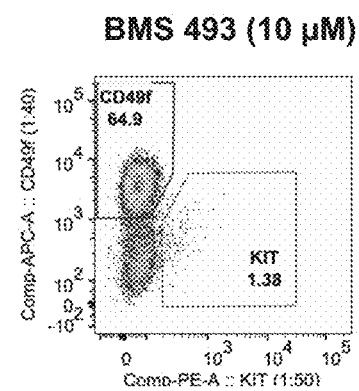
FIG. 7B is a scatter plot displaying the relative content of myoepithelial-like cells and ductal-like cells in a primary in vitro organoid culture of the ACCX5M1 patient-derived xenograft (PDX) line treated with the inverse agonist BMS493 (10 μM) for 7 days and analyzed by flow cytometry.
Figure 7C:
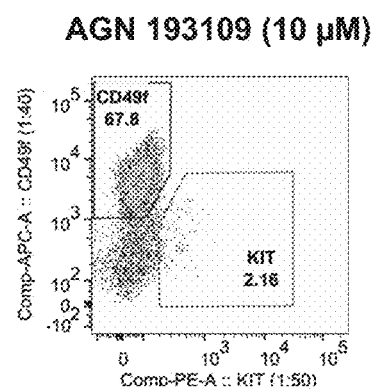
FIG. 7C is a scatter plot displaying the relative content of myoepithelial-like cells and ductal-like cells in a primary in vitro culture of the ACCX5M1 patient-derived xenograft (PDX) line treated with the inverse agonist AGN193109 (10 μM) for 7 days and analyzed by flow cytometry.
Figure 8:
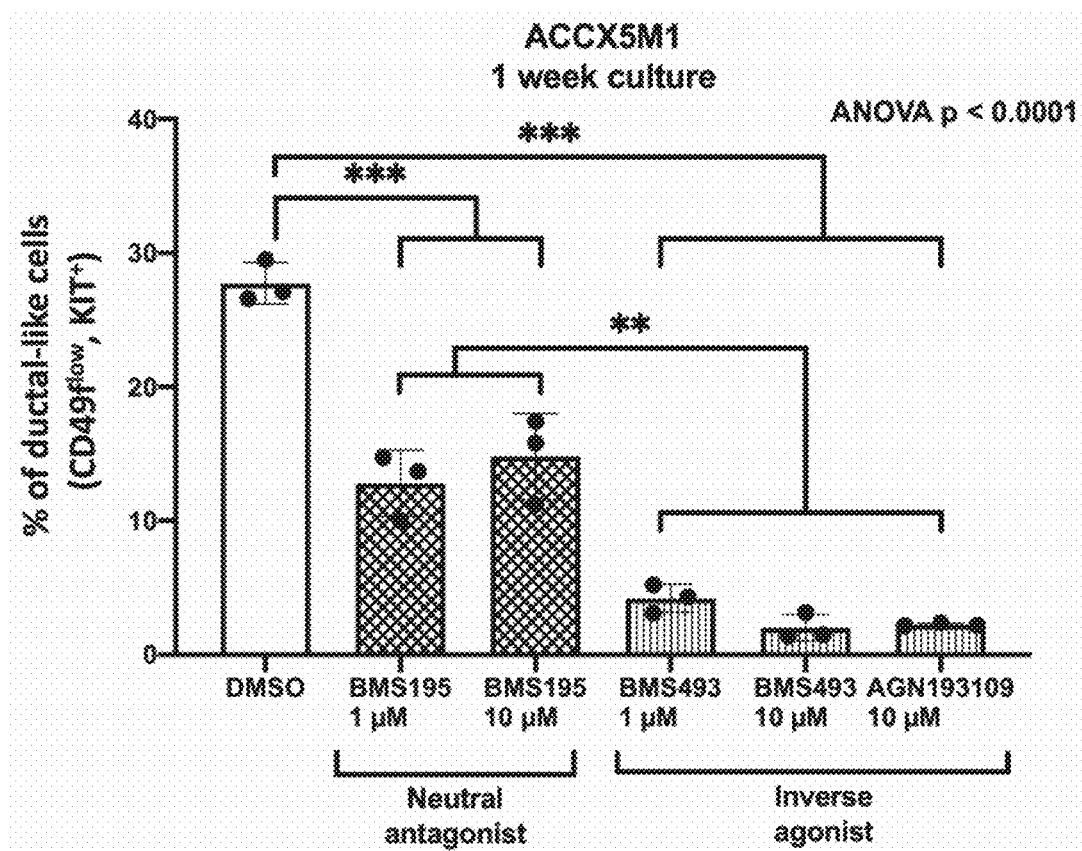
FIG. 8 is a bar graph comparing the percentage of ductal-like ($CD49f^{low}$, $KIT^+$) cells after one week from each of the treatments of FIGS. 6A-7C. Note that BMS195614 has been abbreviated as "BMS195" due to the available space in the Figure.
Figure 9:
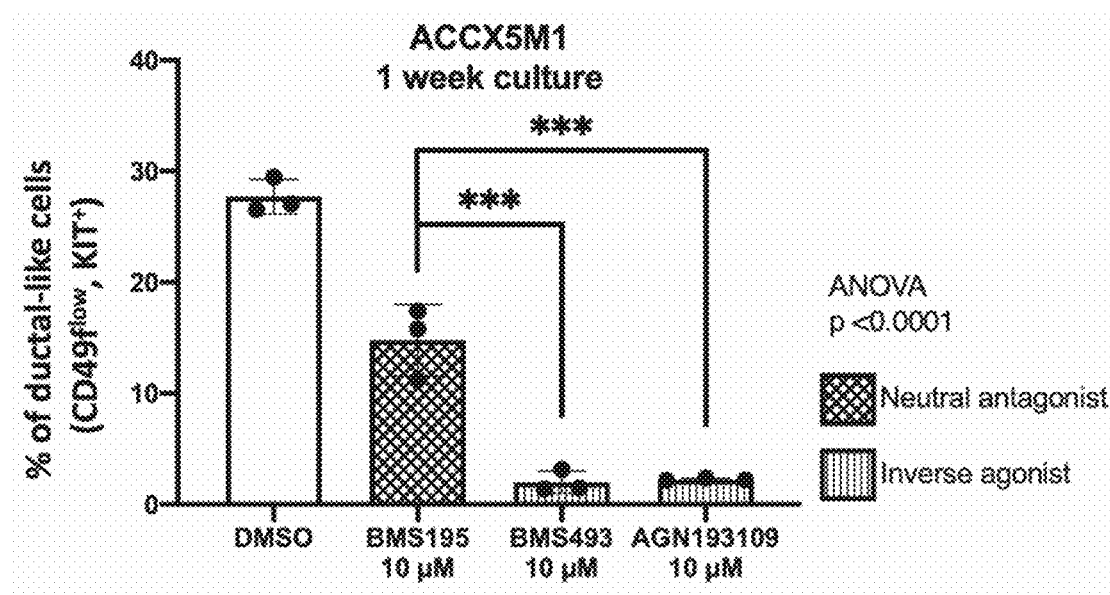
FIG. 9 is a bar graph comparing the percentage of ductal-like ($CD49f^{low}$, $KIT^+$) cells after one week from the treatments of FIGS. 6A, 6C, 7B and 7C. Note that BMS195614 has been abbreviated as "BMS195" due to the available space in the Figure.
Figure 10:
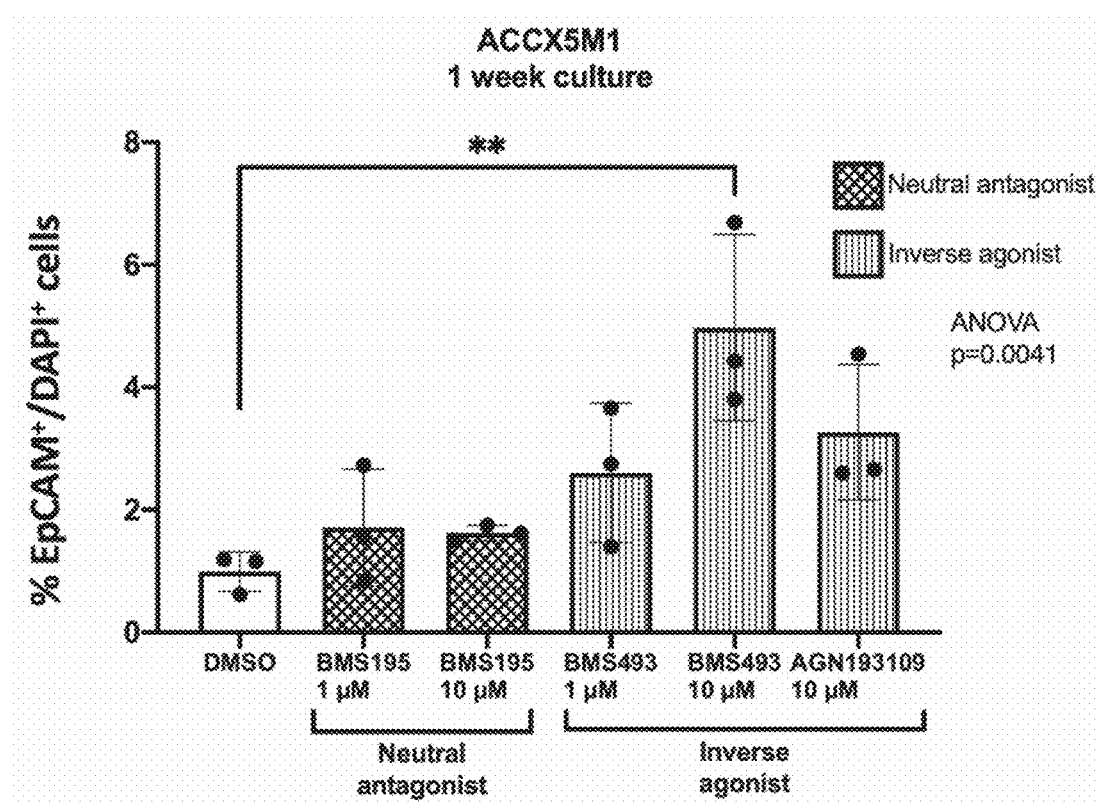
FIG. 10 is a bar graph comparing the percentage of $EpCAM^+/DAPI^+$ cells (i.e. dead epithelial cells) after one week from each of the treatments of FIGS. 6A-7C. Note that BMS195614 has been abbreviated as "BMS195" due to the available space in the Figure.

FIG. 7A is a scatter plot displaying the relative content of myoepithelial-like cells and ductal-like cells in a primary in vitro organoid culture of the ACCX5M1 patient-derived xenograft (PDX) line treated with the inverse agonist BMS493 (1 μM) after one week. FIG. 7B is a scatter plot displaying the relative content of myoepithelial-like cells and ductal-like cells in a primary in vitro organoid culture of the ACCX5M1 patient-derived xenograft (PDX) line treated with the inverse agonist BMS493 (10 μM) for 7 days and analyzed by flow cytometry. FIG. 7C is a scatter plot displaying the relative content of myoepithelial-like cells and ductal-like cells in a primary in vitro organoid culture of the ACCX5M1 patient-derived xenograft (PDX) line treated with the inverse agonist AGN193109 (10 μM) for 7 days and analyzed by flow cytometry. FIG. 8 is a bar graph comparing the percentage of ductal-like (CD49f$^{low}$, KIT$^+$) cells after one week from each of the treatments of FIGS. 6A-7C. FIG. 9 is a bar graph comparing the percentage of ductal-like (CD49f$^{low}$, KIT$^+$) cells after one week from the treatments of FIGS. 6A, 6C, 7B and 7C. FIG. 10 is a bar graph comparing the percentage of EpCAM$^+$/DAPI$^+$ cells (i.e., dead epithelial cells) after one week from each of the treatments of FIGS. 6A-7C. In FIG. 10, a significant increase in the percentage of dead cells can be observed with the inverse agonist BMS493 (10 μM), but not with the neutral antagonist (BMS195614). It should be noted that in FIGS. 8-10, BMS195614 has been abbreviated as "BMS195" due to the available space in the Figures.

In FIG. 8, the increase in concentration of neutral antagonist BMS195614 (from 1 μM to 10 μM) does not translate in a significant decrease in the percentage of ductal-like (CD49f$^{low}$, KIT$^+$) cells, which remains statistically superior to the percentage of ductal-like (CD49f$^{low}$, KIT$^+$) cells observed after treatment with inverse agonists BMS493 and AGN193109. This indicates that the lower anti-tumor activity of the neutral antagonist is not explained by a lower pharmacological potency of BMS195614 as compared to inverse agonists BMS493 and AGN193109. That is, the anti-tumor activity of the neutral antagonist is not expected to improve by further increasing the dose of the drug.

Accordingly, as can be seen from the above, a neutral antagonist such as BMS195614 is unable to reproduce the anti-tumor effects that are observed with the inverse agonists of RAR signaling (i.e., BMS493 and AGN193109). The anti-tumor effect of the antagonist BMS195614 is clearly systematically inferior to that of both inverse agonists BMS493 and AGN193109 at both doses (i.e., 1 µM and 10 µM). As noted above, the fact that the anti-tumor effect of BMS195614 does not increase as the dose is increased from 1 µM to 10 µM indicates that the drug has already reached its maximum theoretical effect, which is inferior to that of both BMS493 and AGN193109. This difference in the maximal anti-tumor effect of the two classes of drugs (i.e., antagonists vs. inverse agonists) is very important, since it shows that not all inhibitors of RAR signaling are therapeutically equivalent, due to fundamental (i.e., qualitative and not quantitative) reasons linked to the way their mechanism of action interferes with the biology of RAR signaling (which then results in a systematic difference in the fraction of cancer cells that the two classes of drugs are able to kill).

It was previously known that, by definition, inverse agonists suppress RAR/RXR signaling below its basal (i.e. constitutive) levels, while antagonists prevent the activation of RAR/RXR signaling above basal (i.e. constitutive) levels induced by direct agonists (i.e., stimulants). Put another way, antagonists can be thought of as agents that act to prevent acceleration of an engine above its idling speed, while inverse agonists actually act to slow the engine and can reduce the engine speed below its idling speed. However, the findings described above are new and novel, as it was not previously known suppression of RAR/RXR signaling below basal (i.e. constitutive) levels is necessary to achieve the killing of certain subsets of cancer cells. The above data and discussion show that the fraction of cancer cells that can be killed using antagonists is significantly lower than the fraction of cancer cells that can be killed using inverse agonists.

The use of inverse agonists to treat tumors is not limited to treating adenoid cystic carcinomas, or to treatment in the absence of other antitumor treatment. Inverse agonists may be used in combination with other antitumor treatments, including without limitation hormone therapy, immunotherapy, anti-angiogenic therapy, pro-differentiation therapies, such as those based on inhibition of lysine-specific de-methylases (KDMs) or isocitrate dehydrogenases (IDHs), therapies based on the inhibition of proliferative or anti-apoptotic signals mediated by tyrosine kinases and/or therapies base on the inhibition of poly(ADP-ribose) polymerases (PARPs). Inverse agonist antitumor treatment also could be used—alone or in combination with one or more other antitumor treatments as mentioned above—for treating other cancerous tumors, including without limitation breast carcinomas, prostate carcinomas, pancreatic carcinomas, all forms of salivary gland carcinomas, lacrimal gland carcinomas, esophageal carcinomas, gastric carcinomas, cholangiocarcinomas and other carcinomas of the biliary tree, hepatocellular carcinomas, carcinomas of the small intestine, colon carcinomas, rectal carcinomas, carcinomas of the sweat glands, lung adenocarcinomas, ovarian carcinomas, carcinomas of the fallopian tubes, endometrial carcinomas, squamous cell carcinomas of the skin, head-and-neck district, lips, mouth, nasal sinuses, pharynx, larynx, esophagus, trachea, bronchi, lungs, uterine cervix, vagina, vulva, penis or anus, bladder carcinomas and other urothelial carcinomas of the renal pelvis, ureter or urethra, neuroendocrine carcinomas of the pancreas, small cell lung carcinomas, and renal cell carcinomas.

It is to be understood that the method of treating adenoid cystic carcinoma is not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of treating adenoid cystic carcinoma, comprising the step of administering an effective dosage of an inverse agonist of retinoic acid receptor (RAR) or retinoid x receptor (RXR) signaling to a patient in need thereof.

2. The method of treating adenoid cystic carcinoma as recited in claim 1, wherein the inverse agonist of retinoic acid receptor (RAR) or retinoid x receptor (RXR) signaling comprises BMS493.

3. The method of treating adenoid cystic carcinoma as recited in claim 1, wherein the inverse agonist of retinoic acid receptor (RAR) or retinoid x receptor (RXR) signaling comprises AGN193109.

4. The method of treating adenoid cystic carcinoma as recited in claim 1, further comprising the step of performing radiotherapy on the patient, either following or concurrently with the administration of the effective dosage of the inverse agonist of retinoic acid receptor (RAR) or retinoid x receptor (RXR) signaling, wherein the inverse agonist of retinoic acid receptor (RAR) or retinoid x receptor (RXR) signaling acts as a radio-sensitizer.

5. The method of treating adenoid cystic carcinoma as recited in claim 1, further comprising the step of performing chemotherapy on the patient, either following or concurrently with the administration of the effective dosage of the inverse agonist of retinoic acid receptor (RAR) or retinoid x receptor (RXR) signaling, wherein the inverse agonist of retinoic acid receptor (RAR) or retinoid x receptor (RXR) signaling acts as a chemo-sensitizer.

6. The method of treating adenoid cystic carcinoma as recited in claim 1, wherein the patient is also administered another form of anti-tumor treatment in addition to the inverse agonist of retinoic acid receptor (RAR) or retinoid x receptor (RXR) signaling.

7. The method of treating adenoid cystic carcinoma as recited in claim 6, wherein the another form of anti-tumor treatment includes a treating agent or regimen intended to provide at least one of the group of treatments consisting of chemotherapy, radiotherapy, hormone therapy, immunotherapy, anti-angiogenic therapy, pro-differentiation therapies, such as those based on inhibition of lysine-specific de-methylases (KDMs) or isocitrate dehydrogenases (IDHs), therapies based on the inhibition of proliferative or anti-apoptotic signals mediated by tyrosine kinases, and/or therapies base on the inhibition of poly(ADP-ribose) polymerases (PARPs).

8. The method of treating adenoid cystic carcinoma as recited in claim 6, wherein the inverse agonist of retinoic acid receptor (RAR) or retinoid x receptor (RXR) comprises at least one of the group of inverse agonists comprising BMS493 and AGN193109.

9. The method of treating adenoid cystic carcinoma as recited in claim 7, wherein the inverse agonist of retinoic acid receptor (RAR) or retinoid x receptor (RXR) comprises at least one of the group of inverse agonists comprising BMS493 and AGN193109.

10. The method of treating adenoid cystic carcinoma as recited in claim 4, wherein the inverse agonist of retinoic acid receptor (RAR) or retinoid x receptor (RXR) comprises BMS493, AGN193109, or a combination thereof.

11. The method of treating adenoid cystic carcinoma as recited in claim 5, wherein the inverse agonist of retinoic acid receptor (RAR) or retinoid x receptor (RXR) comprises BMS493, AGN193109, or a combination thereof.

* * * * *